United States Patent
Spedding et al.

(10) Patent No.: US 12,083,091 B2
(45) Date of Patent: Sep. 10, 2024

(54) INHIBITORS OF GLUCOSYLCERAMIDE DEGRADATION IN THE TREATMENT OF DISEASES OF THE MOTOR UNITS

(71) Applicants: SPEDDING RESEARCH SOLUTIONS, Le Vesinet (FR); UNIVERSITE DE STRASBOURG, Strasbourg (FR); INSERM—INSTITUT NATIONAL DE LA SANTE ET DE LA RECHERCHE MEDICALE, Paris (FR)

(72) Inventors: Michael Spedding, Le Vesinet (FR); Alexandre Henriques, Bischheim (FR); Jean-Philippe Loeffler, Berstett (FR)

(73) Assignees: SPEDDING RESEARCH SOLUTIONS, Le Vesinet (FR); UNIVERSITE DE STRASBOURG, Strasbourg (FR); INSERM—INSTITUT NATIONAL DE LA SANTE ET DE LA RECHERCHE MEDICALE, Paris (FR)

( * ) Notice: Subject to any disclaimer, the term of this patent is extended or adjusted under 35 U.S.C. 154(b) by 996 days.

(21) Appl. No.: 17/036,860

(22) Filed: Sep. 29, 2020

(65) Prior Publication Data
US 2021/0077453 A1    Mar. 18, 2021

Related U.S. Application Data

(63) Continuation of application No. 16/092,749, filed as application No. PCT/EP2017/058705 on Apr. 11, 2017, now abandoned.

(60) Provisional application No. 62/320,728, filed on Apr. 11, 2016.

(51) Int. Cl.
| | |
|---|---|
| *A61K 31/336* | (2006.01) |
| *A61K 31/137* | (2006.01) |
| *A61K 31/19* | (2006.01) |
| *A61K 31/4025* | (2006.01) |
| *A61K 31/4453* | (2006.01) |
| *A61P 21/00* | (2006.01) |

(52) U.S. Cl.
CPC .......... *A61K 31/336* (2013.01); *A61K 31/137* (2013.01); *A61K 31/19* (2013.01); *A61K 31/4025* (2013.01); *A61K 31/4453* (2013.01); *A61P 21/00* (2018.01)

(58) Field of Classification Search
None
See application file for complete search history.

(56) References Cited

U.S. PATENT DOCUMENTS

| | | | |
|---|---|---|---|
| 7,884,115 B2 | 2/2011 | Donello et al. | |
| 2004/0219207 A1* | 11/2004 | Rohnert | A61P 25/16 514/440 |
| 2014/0161896 A1* | 6/2014 | Peer | A61K 9/0043 424/499 |

FOREIGN PATENT DOCUMENTS

DE        4307883 A1     9/1993

OTHER PUBLICATIONS

Dodge et al (Proc Natl Acad Sci USA 112:8100-8105, published online Jun. 8, 2015) (Year: 2015).*
Walden et al (J Biol Chem 282:32655-32664, 2007) (Year: 2007).*
Maegawa et al (J Biol Chem 284:23502-23516, 2009) (Year: 2009).*
International Search Report from International Patent Application No. PCT/EP2017/058705, mailed Jun. 19, 2017.
Written Opinion of the International Searching Authority from International Patent Application No. PCT/EP2017/058705, mailed Jun. 19, 2017.
Brooks et al., "El Escorial Revisited: Revised Criteria for the Diagnosis of Amyotrophic Lateral Sclerosis," ALS and Other Motor Neuron Disorders (2000), 1(5), pp. 293-299.
Chandran et al., "A Systems-Level Analysis of the Peripheral Nerve Intrinsic Axonal Growth Program," Neuron (2016), 89(5), pp. 956-970.
Dauer et al., "Magic Shotgun for Parkinson's Disease?" Brain (2014), vol. 137, pp. 1274-1281.
Dodge et al., "Glycosphingolipids are Modulators of Disease Pathogenesis in Amyotrophic Lateral Sclerosis," PNAS (2015), 112(26), pp. 8100-8105.
Dupuis et al., "Dyslipidemia is a Protective Factor in Amyotrophic Lateral Sclerosis," Neurology (2008), 70(13), pp. 1004-1009.
Dupuis et al., "Evidence for Defective Energy Homeostasis in Amyotrophic Lateral Sclerosis: Benefit of a High-Energy Diet in a Transgenic Mouse Model," PNAS (2004), 101(30), 11159-11164.
Henriques et al., "Amyotrophic Lateral Sclerosis and Denervation Alter Sphingolipids and Up-Regulate Glucosylceramide Synthase," Human Molecular Genetics (2015), 24(25), pp. 1-16.
Nokuchi, J., "Neurotrophic and Neuroprotective Actions of an Enhancer of Ganglioside Biosynthesis," International Review of Neurobiology (2009), vol. 85, pp. 319-336.
Kiaei et al., "Celastrol Blocks Neuronal Cell Death and Extends Life in Transgenic Mouse Model of Amyotrophic Lateral Sclerosis," Neurodegenerative Diseases (2005), 2(5), pp. 246-254.
Korkotian et al., "Elevation of Intracellular Glucosylceramide Levels Results in an Increase in Endoplasmic Reticulum Density and in Functional Calcium Stores in Cultured Neurons," The Journal of Biological Chemistry (1999), 274(31), pp. 21673-21678.

(Continued)

*Primary Examiner* — Craig D Ricci
(74) *Attorney, Agent, or Firm* — Greer, Burns & Crain, Ltd

(57) ABSTRACT

Inhibitors of glucosylceramide degradation, to pharmaceutical compositions containing same and to the use of same in the treatment of diseases of the motor units, such as amyotrophic lateral sclerosis.

3 Claims, 14 Drawing Sheets

(56) References Cited

OTHER PUBLICATIONS

Kuwabara et al., "Axonal Guillain-BarréSyndrome: Concepts and Controversies," Lancet Neurol (2013), 12(12), pp. 1180-1188.
Lattante et al., "Defining the Genetic Connection Linking Amyotrophic Lateral Sclerosis (ALS) with Frontotemporal Dementia (FTD)", Trends in Genetics (2015), 31(5), pp. 263-273.
Ledeen et al., "GM1 in the Nuclear Envelope Regulates Nuclear Calcium Through Association with a Nuclear Sodium-Calcium Exchanger", Journal of Neurochemistry (2007), vol. 103, pp. 126-134.
Martin et al., "Loss of Function of Glucocerebrosidase GBA2 is Responsible for Motor Neuron Defects in Hereditary Spastic Paraplegia", The American Journal of Human Genetics (2013), 92(2), pp. 238-244.
McNeill et al., "Ambroxol Improves Lysosomal Biochemistry in Glucocerebrosidase Mutation-Linked Parkinson Disease Cells", Brain (2014), vol. 137, pp. 1481-1495.
Mitsumoto et al., "Clinical Trials in Amyotrophic Lateral Sclerosis: Why So Many Negative Trials and How Can Trials be Improved?", Lancet Neurol (2014), 13(11), pp. 1127-1138.
Narita et al., "Ambroxol Chaperone Therapy for Neuronopathic Gaucher Disease: A Pilot Study", Annals of Clinical and Translational Neurology (2016), 3(3), pp. 200-215.
Palamiuc et al., "A Metabolic Switch Toward Lipid Use in Glycolytic Muscle is an Early Pathologic Event in a Mouse Model of Amyotrophic Lateral Sclerosis", EMBO Molecular Medicine (2015), 7(5), pp. 526-546.
Palmano et al., "The Role of Gangliosides in Neurodevelopment", Nutrients (2015), 7(5), pp. 3891-3913.
Pelled et al., "The Increased Sensitivity of Neurons with Elevated Glucocerebroside to Neurotoxic Agents can be Reversed by Imiglucerase", Journal of Inherited Metabolic Disease (2000), 23(2), pp. 175-184.
Schmitt et al., "A Plural Role for Lipids in Motor Neuron Diseases: Energy, Signaling and Structure", Frontiers in Cellular Neuroscience (2014), 8(25), pp. 1-10.
Schwarz et al., "A Regulatory Role for Sphingolipids in Neuronal Growth," The Journal of Biological Chemistry (1995), 270(18), pp. 10990-10998.
Siebert et al., "Glucocerebrosidase is Shaking Up the Synucleinopathies," Brain (2014), vol. 137, pp. 1304-1322.
Sultana et al., "Lack of Enzyme Activity in GBA2 Mutants Associated with Hereditary Spastic Paraplegia/Cerebellar Ataxia (SPG46), "Biochemical and Biophysical Research Communications (2015), 465(1), pp. 35-40.
Tsai et al., "GM1 Ganglioside is Involved in Epigenetic Activation Loci of Neuronal Cells", Neurochemical Research (2016), 41(1-2), pp. 107-115.
Wennekes et al., "Glycosphingolipids—Nature, Function, and Pharmacological Modulation", Angewandte Chemie International Edition (2009), 48(47), pp. 8848-8869.
Wills et al., "Hypercaloric Enteral Nutrition in Patients with Amyotrophic Lateral Sclerosis: A Randomised, Double-Blind, Placebo-Controlled Phase 2 Trial", Lancet (2014), 383(9934), pp. 2065-2072.
Wu et al., "Sodium-Calcium Exchanger Complexed with GM1 Ganglioside in Nuclear Membrane Transfers Calcium from Nucleoplasm to Endoplasmic Reticulum", PNAS (2009), 106(26), pp. 10829-10834.
Yu et al., "Functional Roles of Gangliosides in Neurodevelopment: An Overview of Recent Advances", Neurochemical Research (2012), 37(6), pp. 1230-1244.
Blennow et al., "Gangliosides in Cerebrospinal Fluid in 'Probable Alzheimer's Disease'", Archives of Neurology (1991), 48(10), pp. 1032-1035.
Blennow et al., "Differences in Cerebrospinal Fluid Gangliosides Between "Probable Alzheimer's Disease" and Normal Aging", Aging Clinical and Experimental Research (1992), 4(4), pp. 301-306.

\* cited by examiner

INHIBITORS OF GLUCOSYLCERAMIDE DEGRADATION IN THE TREATMENT OF DISEASES OF THE MOTOR UNITS

CROSS-REFERENCE TO RELATED APPLICATIONS

This application is a continuation application of the U.S. patent application Ser. No. 16/092,749 filed Oct. 10, 2018 which is the U.S. National phase application corresponding to PCT/EP2017/058705 which was assigned an international filing date of Apr. 11, 2017 and which claims priority to U.S. Provisional Patent Application 62/320,728 filed Apr. 11, 2016, the entire disclosures of which are expressly incorporated herein by reference.

BACKGROUND

The present invention relates to inhibitors of glucosylceramide degradation, to pharmaceutical compositions containing same and to the use of same in the treatment of diseases of the motor units, such as amyotrophic lateral sclerosis.

Motor neurons are myelinated and their membranes are comprised of mainly neuronal lipids, sphingomyelin, phosphatidylcholine, phosphatidylethanolamine, and phosphatidylserine, each of which may contain varying amounts of acyl phospholipids.

Motor neuron disease is a disorder in which motor neurons degenerate and die. Motor neurons, including upper motor neurons and lower motor neurons, affect voluntary muscles, stimulating them to contract. Upper motor neurons originate in the cerebral cortex and send fibers through the brainstem and the spinal cord, and are involved in controlling lower motor neurons. Lower motor neurons are located in the brainstem and the spinal cord and send fibers out to muscles. Lower motor neuron diseases are diseases involving lower motor neuron degeneration. When a lower motor neuron degenerates, the muscle fibers it normally activates become disconnected and do not contract, causing muscle weakness and diminished reflexes. Loss of either type of neurons results in painless weakness which is a clinical hallmark of motor neuron disease. Muscle atrophy is a characteristic of loss of lower motor neurons.

There are a large number of identifiable motor neuron diseases and demyelinating diseases. The most common diseases of these types are Amyotrophic lateral sclerosis (ALS) and multiple sclerosis (MS), respectively.

Amyotrophic lateral sclerosis (ALS) is a severe neurodegenerative disease and the most frequent motor neuron disease among adults (Brooks, B. R. et al., Amyotroph. Lateral Scler Other Motor Neuron Disord., 2000 December; 1(5):293-9). ALS is characterized by a loss of upper motor neurons in the motor cortex and lower motor neurons located in the brainstem and in the spinal cord. The therapeutic options for ALS remain limited despite extensive preclinical and clinical research leading to more than 50 randomized clinical trials, a wide majority of them aiming to counteract directly neurodegeneration (Mitsumoto H et al., The Lancet Neurology, 2014, vol 13, 1127-1138). Gene mutations are associated with familial and sporadic forms of ALS. Most of the genetic forms of ALS are associated to mutations on genes encoding for superoxide dismutase 1 (SOD1), TAR DNA binding protein of 43-kDa (TDP-43) and fused in sarcoma (FUS), or are related to hexanucleotide repeat expansions in chromosome 9 open reading frame 72 (C9ORF72) (Lattante S. et al., Trends in Genetics, 2015, vol 31, 263-273).

Along with neurodegeneration, a metabolic pathology is present in ALS at central and peripheral levels (Schmitt, F et al. Front. Cell. Neurosci, 2014, vol 8, 25). High incidence of dyslipidemia and hypermetabolism is present in ALS patients. High LDL/HDL ratio and high body mass index are associated with better prognosis or slower disease progression (Dupuis, L. et al., Neurology, 2008, vol 70, 1004-1009). Pilot clinical trials suggest benefits for patients under nutritional diets enriched with lipids (Wills, A.-M. et al., Lancet, 2014, vol 383, 2065-72). Pre-symptomatic SOD1 mice, an animal model for ALS, are hypermetabolic (Dupuis, L et al., Proc. Natl. Acad. Sci. U.S.A, 2004, vol 101, 11159-64), prone to use preferentially lipids as nutrients (Palamiuc, L. et al. EMBO Mol. Med., 2015 Vol 7, 526-46), and survive longer when fed with a high fat diet (Dupuis, L et al., Proc. Natl. Acad. Sci. U.S.A, 2004, vol 101, 11159-64). A drastic deregulation of sphingolipids, particularly of gangliosides, was recently described in the central nervous system of ALS patients at disease endpoint and in presymptomatic SOD1 mice (Henriques, A. et al., Hum. Mol. Genet., 2015, vol 24, 7390-7405 et Dodge, J. C. et al., Proc. Natl. Acad. Sci., 2015, Jun. 30; vol 112(26):8100-5).

Gangliosides are sphingolipids containing one or more sugar moieties and sialic acids. Conversion of ceramide into glucosylceramide is the rate limiting step of the de novo synthesis of the wide majority of gangliosides, which takes place in the Golgi apparatus. Gangliosides are present in tissues and fluids, and are particularly enriched at the cell membrane within the nervous system (Wennekes, T. et al., Angewandte Chemie—International Edition, 2009, vol 48, 8848-8869 et Palmano, K. et al., Nutrients, 2015, vol 7, 3891-3913). The composition of brain gangliosides changes, from simple (e.g. GM3) to complex gangliosides (e.g. GM1a), during neuronal development, which has been connected with increased neurogenesis, synaptogenesis and axonal arborisation (Wu, G. et al., Proc. Natl. Acad. Sci. U.S.A, 2009, vol 106, 10829-10834 et Yu, R. K et al., Neurochemical Research, 2012, vol 37, 1230-1244). GM1a, one of the main ganglioside in the nervous system, is located in different cell compartments. At the nuclear envelope, GM1a interacts with sodium-calcium exchanger to potentiate calcium transfer and regulates gene expression during neuronal development by binding to acetylated histones (Ledeen, R. et al., Journal of neurochemistry, 2007, 103 Suppl, 126-134 et Tsai, Y.-T. et al, Neurochem. Res., 2016, vol 41, 107-115).

Mature nervous system requires gangliosides in lipid rafts and at synapses for maintaining physiological functions. The Guillain-Barré syndrome regroups neuropathies caused by the presence of immune antibodies targeting complex gangliosides. Autoantibodies binding to GM1a or GD1a at nodes of Ranvier or directly at the presynaptic part of the neuromuscular junctions lead to acute motor axonal neuropathy, a sub-type of Guillain-Barré syndrome with severe motor axonal degeneration (Kuwabara, S. et al, The Lancet Neurology, 2013, vol 12, 1180-1188). We have recently shown that neuromuscular junction integrity in SOD1 mice requires functional synthesis of glucosylceramide, precursor of gangliosides, suggesting that glycosphingolipids could be key modulators for ALS severity. In addition, inhibition of glucosylceramide synthesis led to impaired nerve regeneration after peripheral nerve injury (Henriques, A. et al., Hum. Mol. Genet., 2015, vol 24, 7390-7405 et Dodge, J. C. et al., Proc. Natl. Acad. Sci., 2015, vol 1, 201508767).

Amyotrophic lateral sclerosis (ALS) is a progressive neurodegenerative disease wherein the upper motor neurons that run from the cerebral cortex to the spinal cord, and the lower motor neurons that run from the spinal cord to muscles, are selectively damaged. Although it is considered to be a most severe nerve disease, no effective therapy has yet become available. Riluzole is the only FDA- and EMA-approved drug to treat ALS. Apart from riluzol, nutrition and ventilation are proposed to ALS patients.

Spasticity is a relatively minor problem which is caused by upper motor neuron lesion reducing the inhibition of lower motor neurons to such a degree that the muscles are more hypo-than hypertonic. Baclofen is the drug of choice for muscle spasms.

Other motor neuron disorders exhibit symptoms similar to ALS but may have one or more recognizable differences. Kennedy's disease (X-linked spinobulbar muscular atrophy) is an X-linked lower motor neuron disease characterized by progressive muscular atrophy usually beginning in mid-adult life. This disease is distinguished from ALS by the absence of hyperreflexia and spasticity.

Spinal muscular atrophy (SMA), is a group of familial disorders which affect large lower motor neurons. Muscle tissue often exhibits evidence of denervation atrophy. Infantile SMA (SMA I, Werdnig-Hoffman disease) is rapidly fatal, death generally ensuing within the first year of life. Chronic childhood SMA (SMA II) progresses slowly, beginning in childhood. Juvenile SMA (SMA III, Wohlfart-Kugelberg-Welander disease) generally has a late childhood or early adolescence onset and runs a slow course.

Primary lateral sclerosis (PLS) is rare disorder arising sporadically in adults from mid- to late-life. Symptoms include progressive spastic weakness of the limbs with spastic dysarthria and dysphagia. Fasciculations, amyotrophy and sensory changes are absent.

Familial spastic paraplegia (FSP) is a hereditary disease characterized by progressive spastic weakness which begins in the distal lower extremities.

Progressive neural muscular atrophy is a collection of degenerative disorders characterized by progressive weakness and wasting of skeletal muscles combined with sensory changes. The most common example is Charcot-Marie-Tooth (CMT) disease. This and many other progressive neuromuscular atrophy diseases are hereditary.

Although there are some treatments for these diseases, there remains a need in the art for a method of treating motor neuron diseases, which provides for both increased relief of symptoms and at least temporary cessation or even reversal of neuronal damage.

Glucosylceramide (GlcCer) is a ubiquitous eukaryotic glycosphingolipid (GSL) which is present on the cytoplasmic face of cellular membranes and on the cell surface. GlcCer is synthesized by the ceramide-specific glucosyltransferase (UGCG). Glucocerebrosidase (GCase) activity is responsible for the degradation of one sphingolipid, the glucosylceramide. At least two enzymes glucocerebrosidase (GBA or GBA1) as well as by β-glucosidase 2 (GBA2 or nonlysosomal glucosylceramidase) catalyze this reaction. GBA is a lysosomal enzyme and GBA2 is a non-lysosomal and membrane-bound enzyme. The GBA is a lysosomal enzyme, whereas GBA2 is present at the plasma membrane and/or the endoplasmic reticulum.

The most frequently used inhibitors of GCase activity in preclinical experimentations are Conduritol B epoxide (CBE), miglustat (N-butyl-deoxynojirimycin ou NB-DNJ), N-(5-adamantane-1-yl-methoxy-pentyl)-Deoxynojirimycin (AMP-DNM) and Afegostat (isofagomine).

CBE is covalent inhibitor of GBA and GBA2, primarily used to create an induced animal model for Gaucher's disease.

Ambroxol [trans-4-(2-Amino-3,5-dibromobenzylamino) cyclohexanol hydrochloride] is a drug used in the treatment of diseases of the respiratory functions for its expectorant properties (Weiser, *CNS Neurosc Therap*, 2008, vol 14, 1, 17-24.). Ambroxol is also an anti-inflammatory and/or anti-oxidant agent. It has been shown to have protective effects in Parkinson's disease models. Ambroxol is known to block Na+ and Ca2+ channels. Additional effects were reported on glutamatergic receptors (AMPA). More recently, ambroxol was proposed as a chaperon molecule for GBA activity and as an inhibitor of GBA2. A clinical trial with ambroxol in Parkinson's disease patients is currently ongoing with the primary aim to chaperone, and therefore increase, the activity of GBA (*Clinical trial reference: NCT02914366: Ambroxol as a Treatment for Parkinson's Disease Dementia*). Ambroxol is suggested to act as a "chemical" chaperone facilitating β-glucocerebrosidase exit from the endoplasmic reticulum and transport to lysosomes. Chaperones may bind and inhibit GBA1 to enhance enzyme entry into lysosomes, where the chaperone may dissociate from the enzyme in the acidic milieu of the lysosome, effectively increasing the delivery of the enzyme to the lysosome. McNeill et al. (2014) showed that ambroxol treatment increases GBA1 activity by acting as a molecular chaperone, it is thus a critical test of the effectiveness of inhibiting GBA2 in ALS models (Mcneill, A. et al. *Brain*. 2014, vol 137, 1481-95).

Miglustat was developed as an inhibitor of GCS (glucosylceramide synthase) and clinically used for lowering the synthesis of glucosylceramide and for treating Gaucher's disease and Niemann Pick's disease. Miglustat is also, at lower dose, a pharmacological modulator/chaperon of GBA and an inhibitor of GBA2. Miglustat is not able to treat in neuropathic forms of Gaucher's disease (type 2 and 3). However, Miglustat is counter-indicated for individuals with neurological issues.

Similarly to miglustat, isofagomine was developed as an inhibitor of GCS for treating patients with Gaucher's disease. However, isofagomine failed in phase 2 to show efficacy in Gaucher's disease. This molecule is also known to be a GBA2 inhibitor and GBA1 chaperone.

AMP-DNM is a chemical entity used as pharmacological tool for inhibiting GBA2 or GCS activity. GBA2 and the use of AMP-DNM in the treatment of cystic fibrosis are disclosed in US 20090186862 A1.

As mentioned above, deficiencies in GBA and GBA2 result in the accumulation of glucosylceramide, which, in the case of GBA, leads to Gaucher's disease, a genetic disorder affecting the reticuloendothelial system and, in severe cases, the central nervous system. This point is confirmed by Siebert et al (2014) and Dauer et al. (2014) which reviewed the evidence that GBA1 mutations, resulting in low lysosomal GCase activity, are responsible for causing Gaucher's disease, and are also associated with increased risk of developing Parkinson's disease. Thus inhibiting GBA1 has a clear risk of inducing Parkinson's disease (Siebert M et al., *Brain*, 2014, 1304-1322; Dauer et al., *Brain*, 2014, vol 137, 1274-1281).

Dodge, J. C. et al. reported a dysregulation of sphingolipids (including glycosphingolipids) in the central nervous system of ALS patients and SOD1 mice (Dodge, J. C. et al., *Proc. Natl. Acad. Sci.*, 2015, vol 1, 201508767). In addition, Dodge and colleagues demonstrated a negative effect of GCS inhibition (resulting in lower glucosylceramide synthesis) but a beneficial effect on direct injection of a complex glycosphingolipid (GM3) into the CNS of SOD1 mice. The proposed mechanism of action is based on the neuroprotection of gangliosides, such GM3. It is indeed known that complex gangliosides are neuroprotective (Inokuchi, *Advances in Neuropharmacology,* 2009; vol 85:319-36).

A second article, published by the inventors, demonstrate that the inhibition of GCS weakened the integrity of the neuromuscular junction in an animal model of ALS and delayed the regeneration of peripheral motor axons in non-transgenic mice (Henriques et al. Human Molecular Genetics, 2015, 1-16).

Moreover, mutations on the gba2 gene, and therefore full loss of the GBA2 activity, lead to motor axonal impairments in human and animal models of hereditary spastic paraplegia (Martin, E. et al., *Am. J. Hum. Genet.,* 2013, Vol 92, 238-244).

SUMMARY

Surprisingly, the inventors have shown, that the administration of inhibitors of glucosylceramide degradation or a pharmaceutical acceptable salt thereof, can be used in the treatment of diseases of the motor units. Furthermore, some of these inhibitors, such as ambroxol, have been reported to be safe and beneficial in diseases such as Parkinson's disease (McNeill et al, Brain, 2014, vol 137(5): 1481-1495; Dauer and Albin Brain, 2014, vol 137, 1274-1281), More particularly, the inventors have shown that the use of glucosylceramide degradation inhibitors increase spinal level of GM1a in a spinal cord and promotes GM1a signal at neuromuscular junction in ALS Mice. Thus these treatments improve motor function, preserves motor neuron survival and neuromuscular junctions of ALS Mice. Furthermore, another unexpected effect was that the use of glucosylceramide degradation inhibitors improved functional recovery and peripheral nerve regeneration after peripheral nerve injury in non-transgenic mice.

The present invention therefore relates to an inhibitors of glucosylceramide degradation or a pharmaceutical acceptable salt thereof, for use in a method for the treatment of diseases of the motor units.

Within the meaning of the present invention, by "inhibitors of glucosylceramide degradation" is meant a compound which is able to inhibit the activity of glucocerebrosidase (GBA) or which is able to inhibit the activity of β-glucosidase 2 (GBA2) or cytosolic beta-glucosidase (GBA3, or β-glucosidase 3 or glucosylceramidase beta 3) or which is able to inhibit at least one enzyme responsible for GCase activity.

Throughout this application, it is contemplated that the term "compound" or "compounds" refers to the compounds discussed herein and includes precursors and derivatives of the compounds, including acyl-protected derivatives, and pharmaceutically acceptable salts of the compounds, precursors, and derivatives. The invention also includes prodrugs of the compounds, pharmaceutical compositions including the compounds and a pharmaceutically acceptable carrier, and pharmaceutical compositions including prodrugs of the compounds and a pharmaceutically acceptable carrier.

In an advantageous embodiment, the inhibitors of glucosylceramide degradation according to the invention may inhibit the activity of glucocerebrosidase (GBA or GBA1) or the activity of β-glucosidase 2 (GBA2). Said enzymes catalyze the hydrolytic cleavage of the beta-glucosidic linkage of the GlcCer. Alternative names for GBA include GBA1, acid beta-glucosidase, beta-GC, D-glucosyl-N-acylsphingosine glucohydrolase. All these term are equivalent.

By "inhibit, "inhibition" or "inhibiting" is meant a decrease by any value between about 10% and about 90%, or of any value between about 30% and about 60%, or over about 100% the activity of GBA or GBA2 for example the ability to inhibit the cleavage of glucose from GlcCer. In some embodiment one or more of the compounds according to the invention may inhibit a GCase within a specific cellular compartment, such as the endoplasmic reticulum or Golgi apparatus, but may dissociate and no longer inhibit a GCase within another cellular compartment, for example a lysosomal compartment.

In another advantageous embodiments, the inhibitors of glucosylceramide degradation according to the invention may specifically inhibit one enzyme responsible for GCase activity, for example the human non-lysosomal GBA2.

The non-limiting examples of inhibitor of glucosylceramide degradation for use in the present invention include:
- the conduritol B epoxide (CBE) also known as 1,2-anhydro-myo-inositol;
- the MDW933 ([(1 S,2R,3S,4R,5R,6R)-5-({445-(3,5-Dimethyl-1H-pyrrol-2-yl-KN)-5-(3,5-dimethyl-2H-pyrrol-2-ylidene-KN)pentyl]-1H-1,2,3-triazol-1-yl}methyl)-7-oxabicyclo[4.1.0]heptane-2,3,4-triolatoydifluoro)boron) derivate from CBE;
- the Miglustat;
- the NB-DNJ also known as N-butyl-Deoxy Nojirimycin;
- NB-DGJ also known as N-butyl deoxy galactonojirimycin (Ridley et al. *J Biol Chem.* 2013; vol 288(36): 26052-66 and Witte et al. *Nat Chem Biol*, (2010) vol 6(12), 907-913),
- AMP-DNM also known as N-(5-adamantane-1-yl-methoxy-pentyl)-Deoxynojirimycin (Bijl et al. *J Pharmacol Exp Ther.* 2008, vol 326(3):849-55 and Aerts et al. *Philos Trans R Soc Lond B Biol Sci.* 2003, vol 358(1433): 905-914);
- the cyclophellitol;
- the β-thiirane;
- the cyclophellitol aziridine (Kah-Yee Li et al. *Org. Biomol. Chem.,* 2014, vol 12, 7786-7791);
- the Ambroxol also known as trans-4-(2-Amino-3,5-dibrombenzylamino)-cyclohexanol (Maegawa et al. *J Biol Chem.* 2009, vol 284(35):23502-16);
- the Afegostat also known as Isofagomin or (3R,4R,5R)-5-(Hydroxymethyl)-3,4-piperidinediol (Kuriyama et al. *Bioorg Med. Chem,* 2008, Volume 16, Issue 15, 7081-7524);
- the Celastrol also known as tripterine or 3-Hydroxy-9β, 13α-dimethyl-2-oxo-24,25,26-trinoroleana-1(10),3,5, 7-tetraen-29-oic acid (Yang et al. *PNAS,* 2014, vol 111 (1), 249-254);
- the Eliglustat also known as Genz-112638 or N-[(1R,2R)-1-(2,3-Dihydro-1,4-benzodioxin-6-yl)-1-hydroxy-3-(1-pyrrolidinyl)-2-propanyl]octanamide (Shayman et al. *Trans Am Clin Climatol Assoc.* 2013; vol 124: 46-60);
- the GENZ-667161 [Cabrera-Salazar M. A. et al.; PLOS ONE 2012: 7(8)];
- the GENZ-642347 as disclosed in WO2003008399;
- or a pharmaceutical acceptable salt thereof.

In a particularly advantageous embodiment, the inhibitor of glucosylceramide degradation is Conduritol B epoxide or a pharmaceutically acceptable salt thereof.

In another particularly advantageous embodiment, the inhibitor of glucosylceramide degradation is ambroxol or a pharmaceutically acceptable salt thereof.

According to the invention the term "treating" or "treatment" with respect to disease of the motor unit is intended to mean substantially inhibiting, slowing or reversing the progression of the disease of the motor unit, such as reducing or inhibiting motor neuron (MN) death, or improves muscle innervation, or substantially ameliorating one or more clinical symptoms of disease of the motor unit, such as diminished motor function.

In a preferred embodiment, the diseases of the motor units according to the present invention can be Amyotrophic Lateral Sclerosis (ALS), Spinal-Bulbar Muscular Atrophy (SBMA), Primary Lateral Sclerosis (PLS), Guillain-Barré Syndrom, Spinal Muscular Atrophy (SMA) and disorders of the motor units resulting from an accident. As used herein, an "accident" may refers for example to a traffic accident or a domestic accident resulting in peripheral nerve lesions.

Pharmaceutical compositions including an inhibitor of glucosylceramide degradation according to the invention, or for use according to the invention, are contemplated as being within the scope of the invention. In some embodiments, pharmaceutical compositions including an effective amount of inhibitor of glucosylceramide degradation are provided.

As used herein, a "pharmaceutical composition" refers to a preparation of an effective amount of a glucosylceramide degradation inhibitor, as the active ingredient, with other chemical components such as physiologically suitable carriers and excipients. The purpose of a pharmaceutical composition is to facilitate administration of the inhibitor of glucosylceramide degradation to a patient.

Another aspect of the invention relates to a pharmaceutical composition comprising at least an inhibitor of glucosylceramide degradation or a pharmaceutically acceptable salt thereof, as mentioned above, as an active ingredient and at least one pharmaceutically acceptable carrier for use in a method for the treatment of diseases of the motor units. In particularly advantageous embodiment, the pharmaceutical composition of the invention is used for treating Amyotrophic Lateral Sclerosis, Spinal-Bulbar Muscular Atrophy, Primary Lateral Sclerosis, Guillain-Barré Syndrom, Spinal Muscular Atrophy and disorders of the motor units resulting from an accident. As used herein, an "accident" may refers for example to a traffic accident or a domestic accident resulting in peripheral nerve lesions.

The term "pharmaceutically acceptable carrier" refers to a carrier or a diluent that does not cause significant irritation to the patient and does not abrogate the biological activity and properties of the administered active ingredient.

The inhibitor of glucosylceramide degradation of the present invention may be administered in the form of a pharmaceutically acceptable salt. In such cases, pharmaceutical compositions in accordance with this invention may comprise a salt of such an inhibitor of glucosylceramide degradation, preferably a physiologically acceptable salt, which are known in the art.

Pharmaceutically acceptable salts of the inhibitor of glucosylceramide degradation of the present invention may be used as a dosage for modifying solubility or hydrolysis characteristics, or may be used in sustained release or prodrug formulations. Also, pharmaceutically acceptable salts of the inhibitor of glucosylceramide degradation of this invention may include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylene-diamine, chloroprocaine, diethanolamine, procaine, N-benzylphenethyl-amine, diethylamine, piperazine, tris(hydroxymethyl)aminomethane, and tetramethylammonium hydroxide.

According to the present invention, the pharmaceutical composition may be administered by oral or non-oral, e.g., intramuscular, intraperitoneal, intravenous, intracisternal injection or infusion, subcutaneous injection, transdermal or transmucosal routes. In a preferred embodiment of the invention, the pharmaceutical composition is administered by oral.

In some embodiments, a compound or pharmaceutical composition in accordance with this invention or for use in this invention may be administered by means of a medical device or appliance such as an implant, graft, prosthesis, stent, etc. Implants may be devised which are intended to contain and release such compounds or compositions. An example would be an implant made of a polymeric material adapted to release the compound over a period of time. A compound may be administered alone or as a mixture with a pharmaceutically acceptable carrier e.g., as solid formulations such as tablets, capsules, granules, powders, etc.; liquid formulations such as syrups, injections, etc.; injections, drops, suppositories, pessaryies. In some embodiments, compounds or pharmaceutical compositions in accordance with this invention or for use in this invention may be administered by inhalation spray, nasal, vaginal, rectal, sublingual, or topical routes and may be formulated, alone or together, in suitable dosage unit formulations containing conventional non-toxic pharmaceutically acceptable carriers, adjuvants and vehicles appropriate for each route of administration.

In particularly advantageous embodiment, the pharmaceutical composition comprising the inhibitor of glucosylceramide degradation or a pharmaceutically acceptable salt thereof is administered to the patient with a disease of motor unit at a dose of 0.01 to 500 mg/kg of body weight/day. Advantageously, the pharmaceutical composition comprising the inhibitor of glucosylceramide degradation or a pharmaceutically acceptable salt thereof is administered to the patient with a disease of motor unit at a dose of 0.1 to 250 mg/kg of body weight/day.

It will be understood that the specific dose level and frequency of dosage for any particular patient may be varied and may depend upon a variety of factors including the activity of the specific compound used, the metabolic stability and length of action of that compound, the age, body weight, general health, sex, diet, mode and time of administration, rate of excretion, drug combination, the severity of the particular condition, and the patient undergoing therapy.

In another aspect, the present invention relates to an inhibitor of glucosylceramide degradation or a pharmaceutical acceptable salt thereof, for use in a method for the treatment of amyotrophic lateral sclerosis.

In another aspect, the present invention relates to the use of glucosylceramide degradation inhibitor for treating trophic lateral sclerosis (ALS) which involves administering to a patient suffering from ALS an effective amount of an inhibitor of glucosylceramide inhibitor. In addition the present invention further provides for the use of an inhibitor of glucosylceramide degradation for increases level of GM1a in the neuromuscular junction and promote the neuroprotection in an ALS patient.

In alternative embodiments, in the treatment of ALS, an appropriate dosage level may generally be about 0.01 to 500 mg per kg subject body weight per day, and may be administered in single or multiple doses. In some embodiments, the dosage level may be about 0.1 to about 250 mg/kg per day. It will be understood that the specific dose level and frequency of dosage for any particular patient may be varied and may depend upon a variety of factors including the activity of the specific compound used, the metabolic stability and length of action of that compound, the age, body weight, general health, sex, diet, mode and time of administration, rate of excretion, drug combination, the severity of the particular condition, and the patient undergoing therapy.

In another aspect, the present invention relates to a method for treating ALS comprising administering, to a patient suffering from ALS, a therapeutically effective amount of at least one inhibitor of glucosylceramide (also known as glycolipid glucocerebroside or GlcCer) degradation.

In another aspect, the present invention relates to an inhibitor of glucosylceramide degradation or a pharmaceutical acceptable salt thereof, for use in a method for the treatment of Spinal-Bulbar Muscular Atrophy.

In another aspect, the present invention relates to a method for treating Spinal-Bulbar Muscular Atrophy comprising administering, to a patient suffering from Spinal-Bulbar Muscular Atrophy, a therapeutically effective amount of at least one inhibitor of glucosylceramide (also known as glycolipid glucocerebroside or GlcCer) degradation.

In another aspect, the present invention relates to an inhibitor of glucosylceramide degradation or a pharmaceutical acceptable salt thereof, for use in a method for the treatment of Primary Lateral Sclerosis.

In another aspect, the present invention relates to a method for treating Primary Lateral Sclerosis comprising administering, to a patient suffering from Primary Lateral Sclerosis, a therapeutically effective amount of at least one inhibitor of glucosylceramide (also known as glycolipid glucocerebroside or GlcCer) degradation.

In another aspect, the present invention relates to a method for treating Guillain-Barré Syndrom comprising administering, to a patient suffering from Guillain-Barré Syndrom, a therapeutically effective amount of at least one inhibitor of glucosylceramide (also known as glycolipid glucocerebroside or GlcCer) degradation.

In another aspect, the present invention relates to a method for treating Guillain-Barré Syndrom comprising administering, to a patient suffering from Guillain-Barré Syndrom, a therapeutically effective amount of at least one inhibitor of glucosylceramide (also known as glycolipid glucocerebroside or GlcCer) degradation.

In another aspect, the present invention relates to an inhibitor of glucosylceramide degradation or a pharmaceutical acceptable salt thereof, for use in a method for the treatment of Spinal Muscular Atrophy.

In another aspect, the present invention relates to a method for treating Spinal Muscular Atrophy comprising administering, to a patient suffering from Spinal Muscular Atrophy, a therapeutically effective amount of at least one inhibitor of glucosylceramide (also known as glycolipid glucocerebroside or GlcCer) degradation.

In another aspect, the present invention relates to an inhibitor of glucosylceramide degradation or a pharmaceutical acceptable salt thereof, for use in a method for the treatment of others disorders of the motor units.

In another aspect, the present invention relates to a method for treating others disorders of the motor units, comprising administering, to a patient suffering from others disorders of the motor units, a therapeutically effective amount of at least one inhibitor of glucosylceramide (also known as glycolipid glucocerebroside or GlcCer) degradation.

For all the above mentioned diseases, an appropriate dosage level may generally be about 0.01 to 500 mg per kg subject body weight per day, and may be administered in single or multiple doses. In some embodiments, the dosage level may be about 0.1 to about 250 mg/kg per day. It will be understood that the specific dose level and frequency of dosage for any particular patient may be varied and may depend upon a variety of factors including the activity of the specific compound used, the metabolic stability and length of action of that compound, the age, body weight, general health, sex, diet, mode and time of administration, rate of excretion, drug combination, the severity of the particular condition, and the patient undergoing therapy.

BRIEF DESCRIPTION OF THE FIGURES

FIG. 1A. Representative pictures of ChAT (left panel) and GM1a (right panel) staining in the ventral horn of the spinal cord. Dashed lines delimited the motor neuron pool. Scale bar=50 µm. FIG. 1B. Mean intensity for GM1a staining at the spinal motor neuron pool (n=6 WT; n=10 SOD1; **p<0.01). FIG. 1C. Representative pictures of GM1 staining in muscle fibers, after staining with cholera toxin subunit B (CTB, middle) and bungarotoxin (BTX, left panel). Merging is provided (right panel) with counter staining of nucleus.

FIG. 4A. Total GCase activity in the spinal cord after CBE treatment. FIG. 4B. Body mass evolution upon treatment. FIG. 4C. Muscle strength evolution upon treatment.

FIG. 5A. Kaplan-Meier showing time to onset of muscle strength loss in SOD1 mice compared to wild-type (WT) mice. FIGS. 5B-5E. Catwalk analysis showing representative pattern of strides of symptomatic SOD1 mice and WT mice with or without CBE treatment 10 mg/kg/day; (FIG. 5B), average speed (FIG. 5C), paw swing (FIG. 5D) and stride length (FIG. 5E). FIG. 5F. Frequency of denervation in muscles of SOD1 mice, at 95 days of age.

FIG. 6A. Representative pictures of spinal motor neurons, after immunostaining with choline acetyl transferase (ChAT, red). Scale bar=50 µm. FIG. 6B. Quantification of cells located in the ventral horn of the spinal cord and having a diameter bigger than 400 µm² (n=10/group, * p<0.05; , p<0.005). FIG. 6**C. Representative pictures of fully innervated (arrows), partially denervated (#) and denervated (*) neuromuscular junctions, after immunostaining with neurofilament and synaptophysin antibodies (green) and bungarotoxin (red). FIG. 6D. Neuromuscular junction integrity (n=10/group, * p<0.05; , p<0.005). FIG. 6E. Representative pictures of post-synaptic part of the neuromuscular junctions with either a normal ganglioside distribution (left panel) or a loss of ganglioside staining (right panel). FIG. 6F. Proportion of neuromuscular junction showing normal ganglioside distribution (n=10/group, *, p<0.001).

FIG. 7A. Kaplan-Meier showing time to observable toe spreading after sciatic nerve injury. FIG. 7B. Representative pictures of the areas of hind limb paws when in contact with the ground. FIGS. 7C-7D. Catwalk analysis of maximal contact area (FIG. 7C) and step cycle (FIG. 7D) of hind paws. FIG. 7E. Muscle strength of ipsilateral hind paws, after sciatic nerve injury. FIG. 7F. Frequency of denervation events in mice, twelve days after injury. FIG. 7G. Gene regulation after CBE treatment and peripheral nerve injury. *,p<0.05; **, p<0.01, #, p value when comparing two contralateral sides.

FIG. 8A. Representative pictures of ventral horn of spinal cord after GFAP staining. FIG. 8B. Mean intensity per pixel in the ventral horn of the spinal cord, in SOD1 mice and wild type littermates.

FIGS. 9A-9B. Unsupervised clustering performed with the 500 transcripts showing the highest variability of expression among groups, in the spinal cord (FIG. 9A) and in muscle (FIG. 9B). FIG. 9C. Venn diagram showing the number of deregulations in muscle, between WT and SOD1 groups, and SOD1 and SOD1-CBE groups. FIG. 9D. Venn diagram showing the number of deregulations in spinal cord, between WT and SOD1 groups, and SOD1 and SOD1-CBE groups.

FIG. 10B. Disease onset of SOD1 mice when the treatment starts at day 75 of age (n=11/12 per group). FIG. 10C. Neuromuscular junctions (NMJs) integrity in SOD1 mice after ambroxol administration, at 95 days of age. FIG. 10D. Muscle strength of non-transgenic and SOD1 mice, when the treatment is initiated at a symptomatic disease stage (n=5-6/group, p value<0.05). FIG. 10E. Survival of SOD1 mice receiving ambroxol during their symptomatic disease stage (n=5-6/group, p value<0.05). FIG. 10F. Muscle strength of ipsilateral hind paws, after sciatic nerve injury (n=10/group, p value<0.05). FIG. 10G. Percentage of correct muscle innervation in mice, ten days after injury (n=10/group, p value<0.05).

EXAMPLES

Material and Method

Figure 1A:
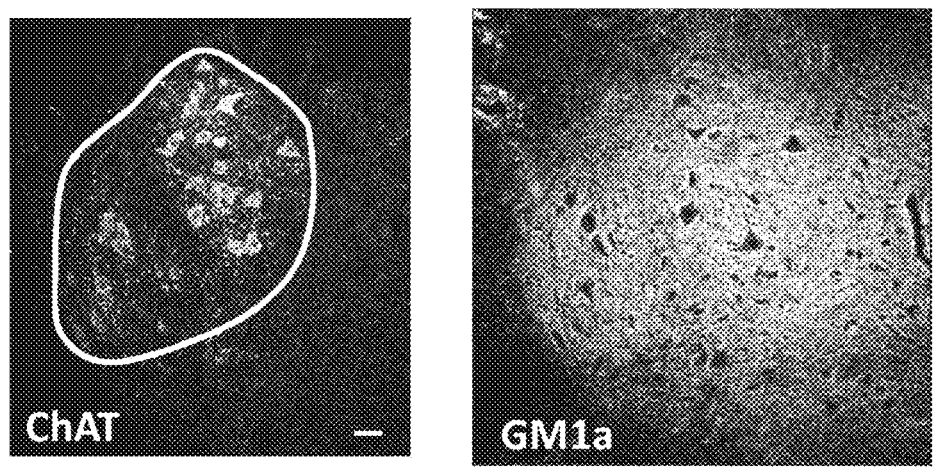
FIGS. 1A-1C: Abnormal distribution of GM1 within the motor unit of SOD1 mice, at early symptomatic stage.

Mice: Experiments followed current European Union regulations (Directive 2010/63/EU) and were performed by authorized investigators (No. A67-402 to A.H.), after approval by the ethics committee of the University of Strasbourg (license APAFIS 2255 and APAFIS 622).

SOD1 mice: FVB/N male mice, overexpressing the SOD1 (G86R) protein, were maintained in our animal facility at 23° C. with a 12 hours light/dark cycle. Mice had access to water and to regular A04 rodent chow ad libitum. Glucosylceramide degradation was inhibited with conduritol B epoxide (CBE, 10 mg/kg/day, Cayman chemical, Ann Arbor, USA) or with ambroxol (120-150 mg/kg/day). CBE was given on a daily basis by intraperitoneal injections. Ambroxol was given orally in the drinking water. The placebo groups received the vehicle, consisting in NaCl 4% or regular water. The treatment started at 75 days of age and stopped at 95 days of age. Non-transgenic littermates served as controls. Body mass and muscle strength (Grip test, Bioseb, Chaville, France) of individual hind limbs were analyzed on a daily basis. The locomotor profiles of mice were analyzed with a catwalk device (Noldus). Mice were habituated to the device at 85 days of age, and consisted in free exploration, followed by three consecutive measurements. At 94 days of age, the locomotor profiles were recorded at least three times per mice. Average speed, paw swing and stride length were measured. After deep anesthesia induced by sodium pentobarbital (120 mg/kg), 95 days old mice were sacrificed and lumbar spinal cord and gastrocnemius and tibialis anterior muscles were dissected. Tissues dedicated to biomolecular analysis were directly snap frozen in liquid nitrogen at stored at −80° C. For histological analysis, tissues were either fixed 1 hours in paraformaldehyde 4% or stored in PBS at 4° C., or snap frozen in isopentane and stored at −80° C. until further use. At 95 days of age, SOD1 mice presented with motor impairments, as determined by visual examination and electromyography. Non-transgenic littermates served as controls.

Sciatic Nerve Injury: Peripheral nerve injury was performed in order to induce muscle denervation and axonal regeneration. Non-transgenic mice were anesthetized with ketamine chlorohydrate (100 mg/kg) and xylazine (5 mg/kg). The sciatic nerve was exposed at mid-thigh level and crushed with fine forceps for 30 s. The skin incision was sutured, and mice were allowed to recover. The hind limb, contralateral to the lesion, served as control. Mice were treated with CBE (10 mg/kg/d) for 12 days, or with ambroxol (120-150 mg/kg/day) for 10 days, starting the day before surgery. Mice were followed on a daily basis. Body mass, muscle strength of individual hind limbs (mean of three tests was recorded), and locomotor profile (catwalk, Noldus) were analyzed.

Histology:

Spinal cord: Lumbar spinal cord fixed in paraformaldehyde 4% were used for studying the distribution of GM1a around motor neurons. Coronal section 40 µm thick were realized with a vibratome and were stained with an anti-choline acetylcholine transferase (1/100, Millipore, France) and an alexa594 conjugated goat (1/200, Jackson) antibodies. GM1a was detected with the cholera toxin sub-unit beta coupled with an Allexa488 dye (1/200, ThermoFisher). Fluorescence intensity of GM1a was calculated with an image processing program (ImageJ). For motor neuron couting, all neurons located in the ventral horn, that were >400 µm² in size and ChAT positive were considered as alpha motor neurons. Six sections of spinal cord that were apart over a length of 0.24 mm were counted.

Muscle bundles: Tibialis anterior muscles fixed in paraformaldehyde 4% were dissected into bundles under a binocular microscope. Bundles were collected from at least three different parts of the muscle. Acetylcholine receptors in the postsynaptic apparatus of neuromuscular junctions were labeled with rhodamine-conjugated α-bungarotoxin (Sigma-Aldrich). Immunofluorescent labeling of nerve terminals was performed with a rabbit polyclonal anti-synaptophysin antibody diluted 1/200 (Abcam, Cambridge, UK), and Alexa conjugated goat anti-rabbit diluted 1/500 (Jackson). Neuromuscular junction integrity was assessed by studying the colocalization of synaptophysin and bungarotoxin signal. Effect of CBE on GM1a at the neuromuscular junction was determined by labelling muscle bundles with cholera toxin sub-unit beta coupled with an Allexa488 dye (1/200, ThermoFisher) and the rhodamine-conjugated α-bungarotoxin.

Coronal muscle sections: Twenty-micrometer sections were obtained by cutting isopentane fresh-frozen tibialis anterior muscles perpendicular to the muscle axis with a cryostat at −20° C. (Leica, Nanterre, France). Acetylcholine receptors in the postsynaptic apparatus of neuromuscular junctions were labeled with rhodamine-conjugated α-bungarotoxin (Sigma-Aldrich). GM1a distribution was labeled with the cholera toxin sub-unit beta coupled with an Allexa488 dye (1/200, ThermoFisher).

Statistics: Data was expressed as the mean±SEM and were analyzed with PRISM 6.0b (GraphPad, San Diego, CA). Student's t test was used to compare two groups, and ANOVA followed by Fisher's LSD test was applied to compare more than two groups. Times to events were analyzed with Log-rank test. Differences with P-values of <0.05 were considered significant.

Example 1: Ganglioside Pathology in ALS

The metabolism of glycosphingolipids is deregulated at disease end stage, in spinal cord tissues from ALS patients stage [Dodge et al. 2015 PNAS]. The expression of UGCG, a gene coding for an enzyme catalyzing the first synthetic step of gycosphingolipid metabolism, was strongly upregulated in muscle biopsies of ALS patients, independently of disease stage (Henriques et al., Human Molecular Genetics, 2015, 1-16), suggesting that gangliosides are deregulated at early disease stage, at least at the distal part of the motor unit.

The four main gangliosides, GM1a, GD1a, GD1b and GT1b are present in the cerebrospinal fluid of healthy individuals and neurological patients (Blennow, K. et al. *Arch Neurol* 48, 1032-1035 (1991), Blennow, K. et al. *Aging (Milano.)* 4, 301-306 (1992). The levels of sphingolipids in the cerebrospinal fluid in human depend, at least partially, on ageing process and by neurological disorders.

Figure 1B:
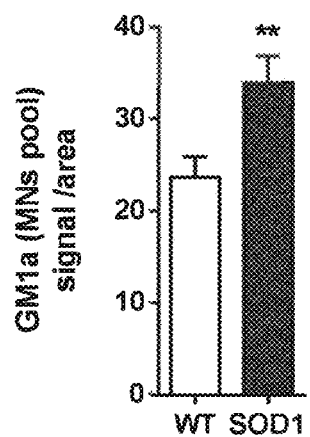

GM1a distribution was studied in the spinal cord of SOD1 mice, an animal model of ALS. GM1a signal was closely associated with axonal structures on spinal cord section. Intensity of GM1a signal at the motor neuron pool was stronger in symptomatic SOD1 mice, compared to non-transgenic mice (FIGS. 1A-1B).

Figure 2:
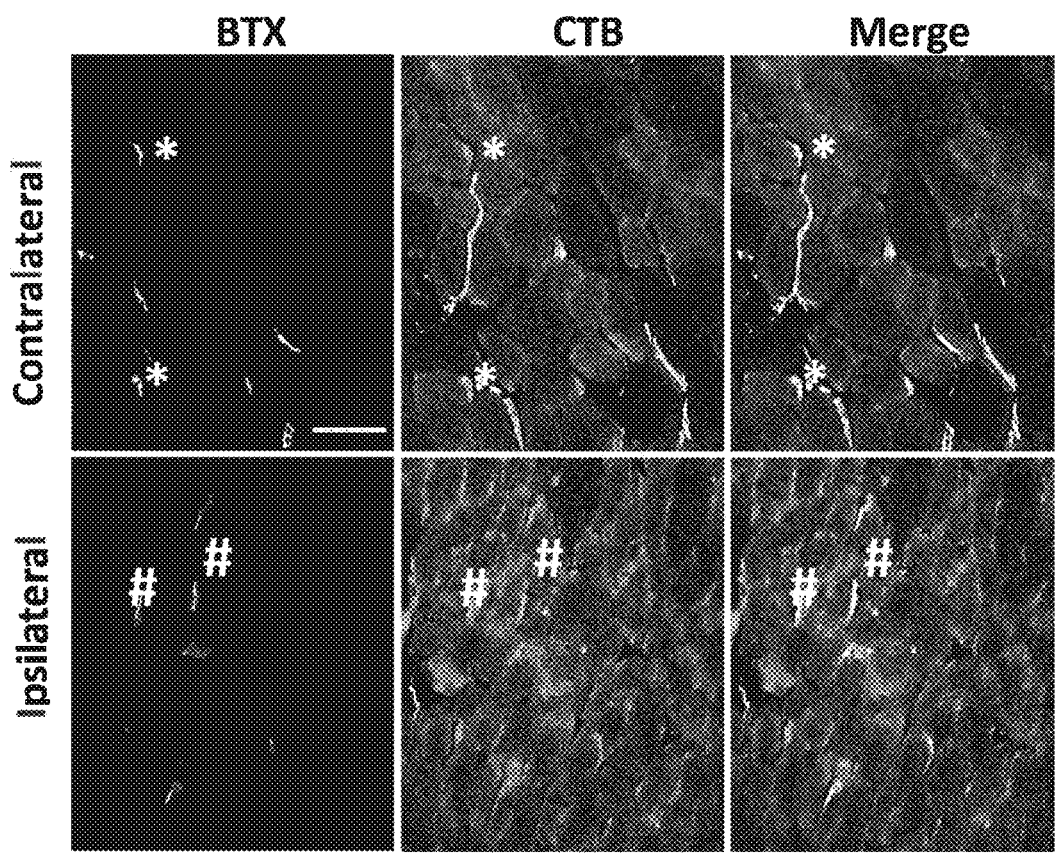
FIG. 2: Loss of gangliosides in peripheral axons and at the neuromuscular junction after sciatic nerve injury. Left panels show post-synaptic apparatus of the neuromuscular junctions (labelled with labelled bungarotoxin, BTX). Choleral toxin subunit B signal (CTB, shown in the middle panels) is observed in axons and at the synapse of the neuromuscular junctions in non-transgenic mice (*). Only a weak signal very close to the neuromuscular synapse is noticed in early symptomatic SOD1 mice (#). Merged images are presented (right panel). Scale bar 100 µm.

At the distal part of the motor unit, GM1a was closely associated to axons innervating to the neuromuscular synapses. GM1a was not detected in muscle fibers, at the exception of the post-synaptic part of the neuromuscular junction, where GM1a-positive dots are visible. GM1a signal was present along the neurofilament signal, also both signal did not co-localized. Experimental denervation induced by peripheral nerve injury, lead 2 days after injury, to severe loss of GM1a signal in muscle from the ipsilateral side of injury (FIG. 2).

Figure 1C:
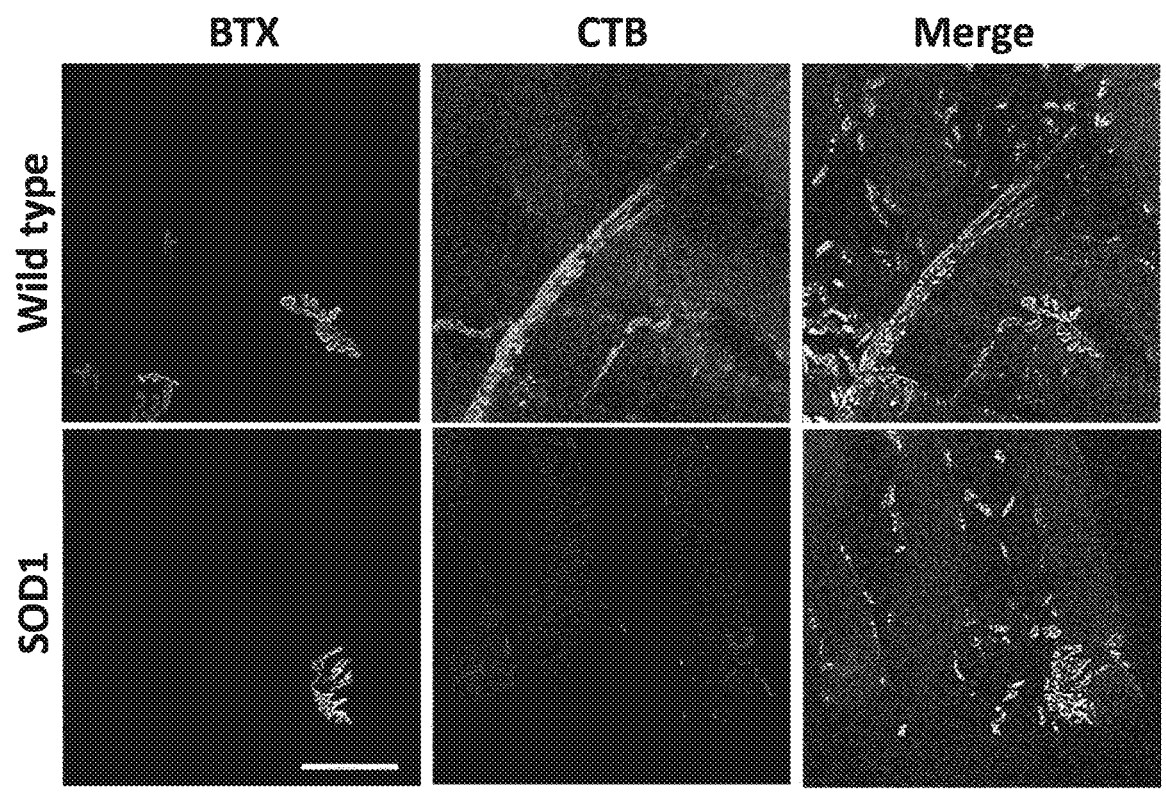
Figure 3:
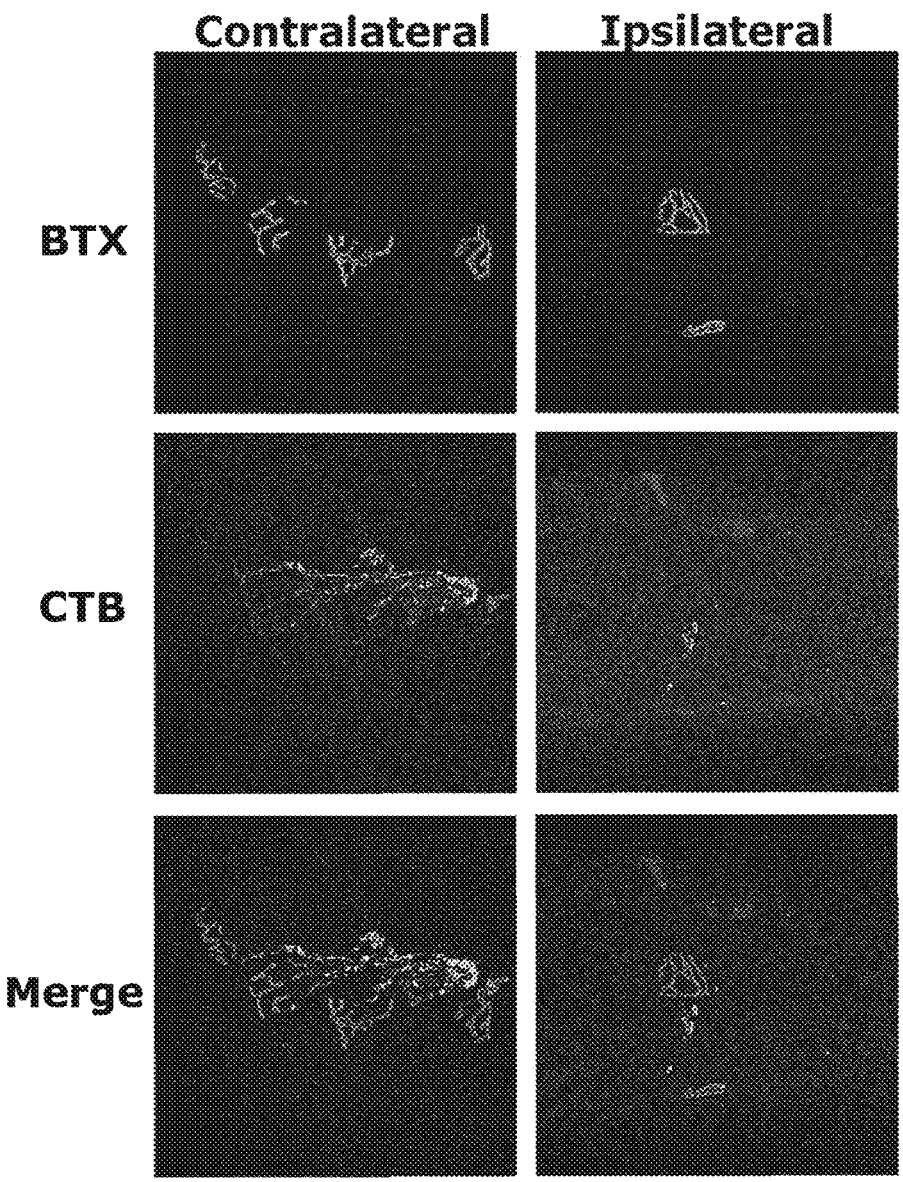
FIG. 3: Loss of gangliosides in peripheral axons and at the neuromuscular junction after sciatic nerve injury. Staining was performed using the labelled bungarotoxin (BTX), which labels the post-synaptic part of the neuromuscular junction and the labelled cholera toxin subunit B (CTB), which labels the gangliosides, Scale bar 50 µm. Contralateral, uninjured nerve; Ipsilateral, injured nerve.

In SOD1 mice, many neuromuscular junctions presented with reduced or absent GM1a signal. We noted less GM1a-positive axons and less GM1a-positive dots at the neuromuscular synapses (FIG. 1C; FIG. 3). Similarly, in early symptomatic TDP-43 mice, GM1a signal was normally present at the motor axons, but less frequently associated with the neuromuscular junction.

Early deregulation of gangliosides at the neuromuscular junctions suggests that gangliosides are part to the motor unit stress in ALS. Taken together, these results demonstrate that gangliosides and GM1a in particular, is deregulated in ALS, with increased levels in the central nervous system, and by decrease at the neuromuscular junctions in animal models at early disease stage.

Figure 4A:
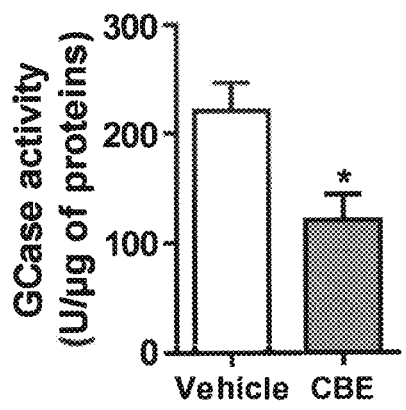
FIGS. 4A-4C: Conduritol B epoxide (CBE) downregulates GCase activity in the spinal cord and does not induce side effects.
Figure 4B:
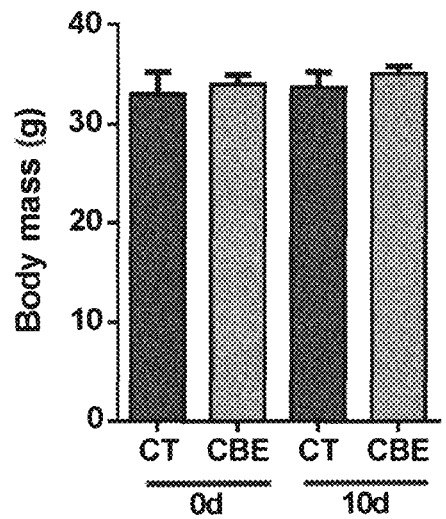
Figure 4C:
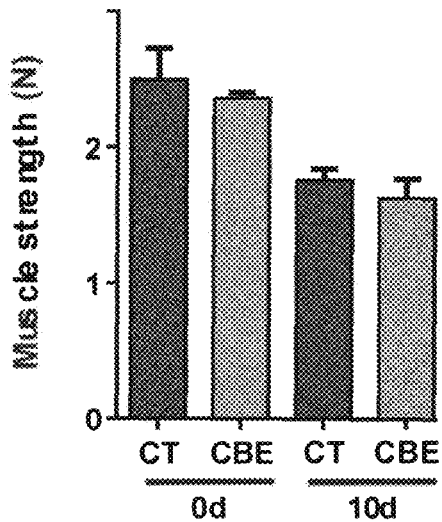

Example 2: Conduritol B Epoxide Delays Disease Onset, Improves Motor Functions and Promote Neuromuscular Junction Integrity in SOD1 Mice The synthesis of glucosylceramide is the entry point into the ganglioside pathway and is required for the development and maturation of the central and peripheral nervous system. Pharmacological inhibition of the synthesis of glucosylceramide, weakens the neuromuscular junctions and hasten disease progression in SOD1 mice (Henriques, A. et al., *Hum. Mol. Genet.*, 2015, vol 24, 7390-7405 et Dodge, J. C. et al., *Proc. Natl. Acad. Sci.*, 2015, Jun. 30; vol 112(26): 8100-5). Here, the inventors sought to promote the de novo synthesis of ganglioside by inhibiting GBA, the enzyme responsible for the degradation of glucosylceramide, with conduritol B epoxide (CBE). The objective was to study the CBE effects on disease onset in SOD1 mice. Presymptomatic SOD1 mice and non-transgenic littermates were treated with CBE (10 mg/kg/day), a dose able to decrease GCase activity in the spinal cord without inducing loss of motor function in non-transgenic mice (FIGS. 4A-4C).

Figure 5A:
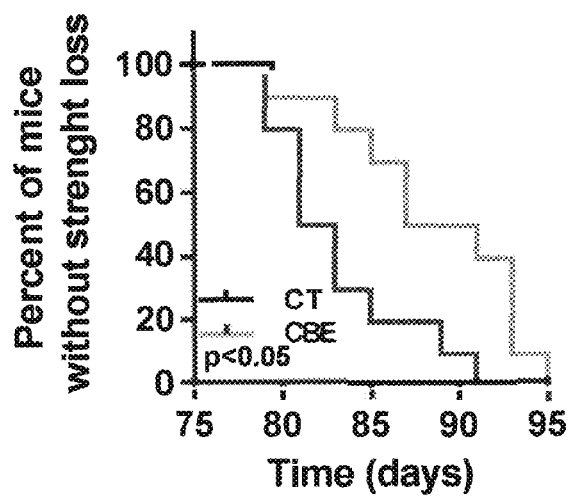
FIGS. 5A-5F: Pharmacological inhibition of glucosylceramide degradation delays disease onset and improves motor functions in SOD1 mice.
Figure 5B:
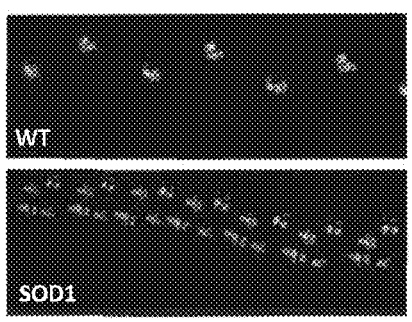
Figure 5C:
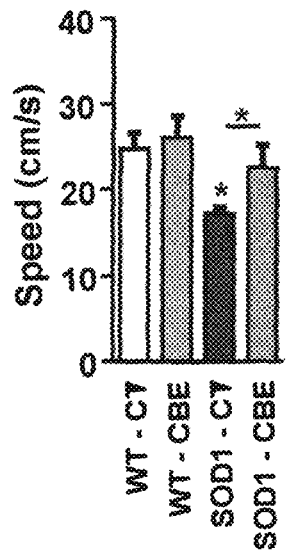
Figure 5D:
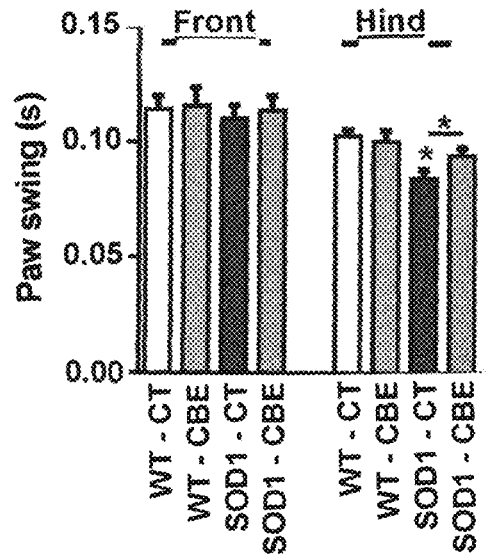
Figure 5E:
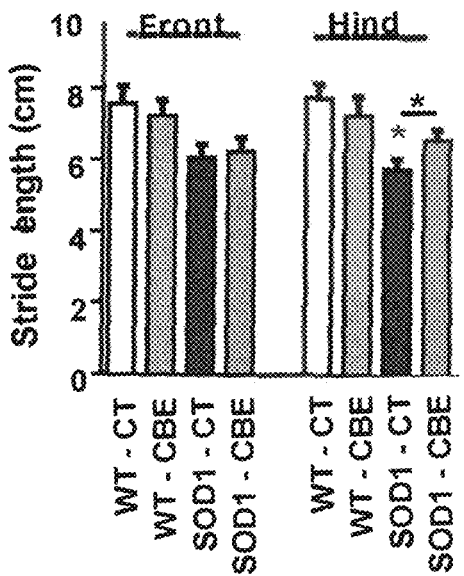
Figure 5F:
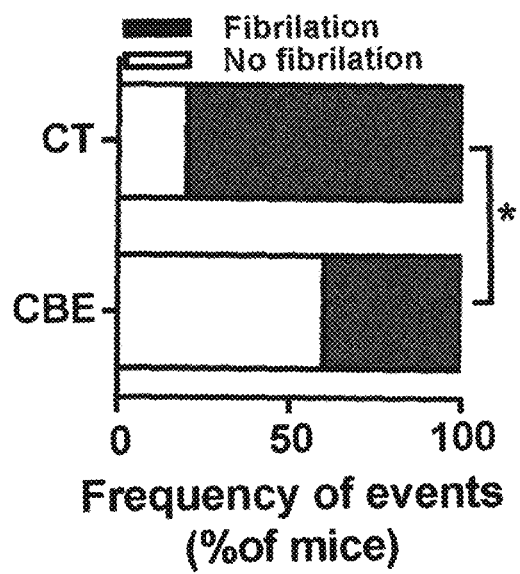

Muscle strength and locomotion profile of SOD1 mice were monitored to detect early signs of disease onset. Disease onset, defined by the onset of muscle strength loss, was significantly delayed by 6 days in SOD1 mice treated with CBE compared to the placebo group (FIG. 5A). Gait analysis revealed that SOD1 at 95 days of age presented with reduced average speed, reduced stride length and paw swing, compared to non-transgenic littermates. CBE treatment completely prevented the development of locomotor impairments in SOD1 mice (FIGS. 5B-5E). Electromyogram revealed that fibrillation events, a sign of muscle denervation, were less frequently detected in SOD1 mice upon CBE treatment, when compared to the SOD1 placebo group (FIG. 5F).

Figure 6A:
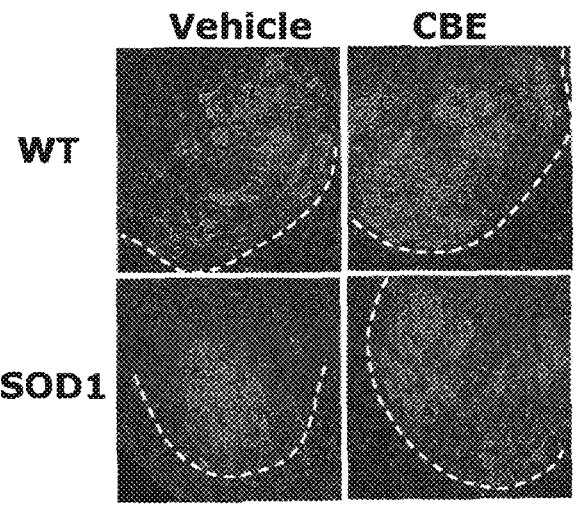
FIGS. 6A-6F: Pharmacological inhibition of glucosylceramide degradation promotes neuroprotection and improves muscle innervation.
Figure 6B:
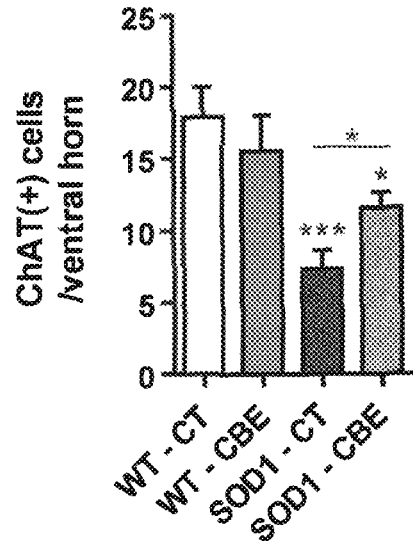
Figure 8A:
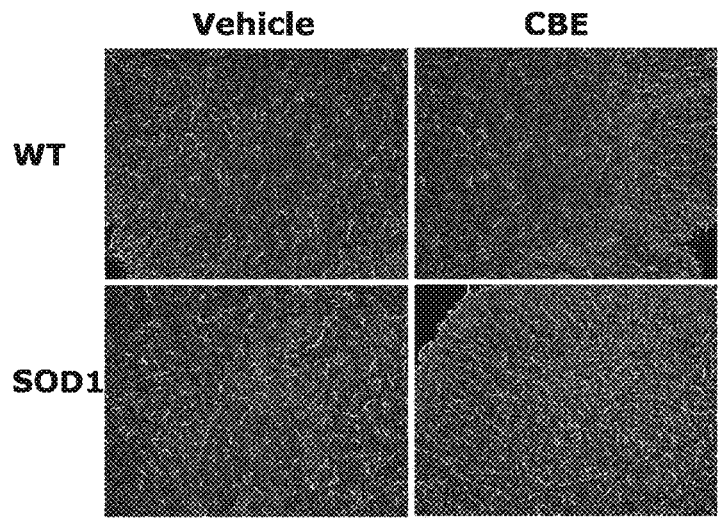
FIGS. 8A-8B: CBE treatment had no influence on the activation of astrocytes.
Figure 8B:
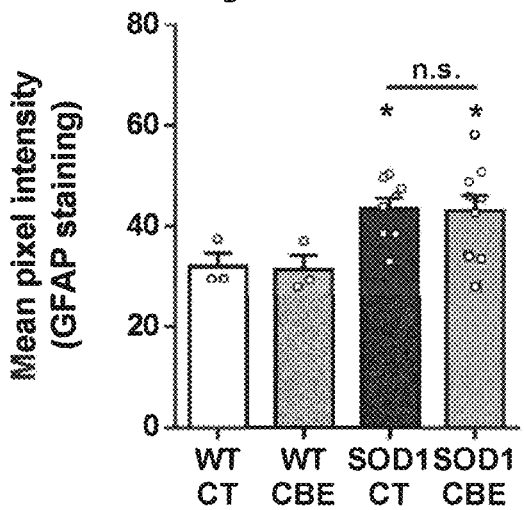
Figure 9A:
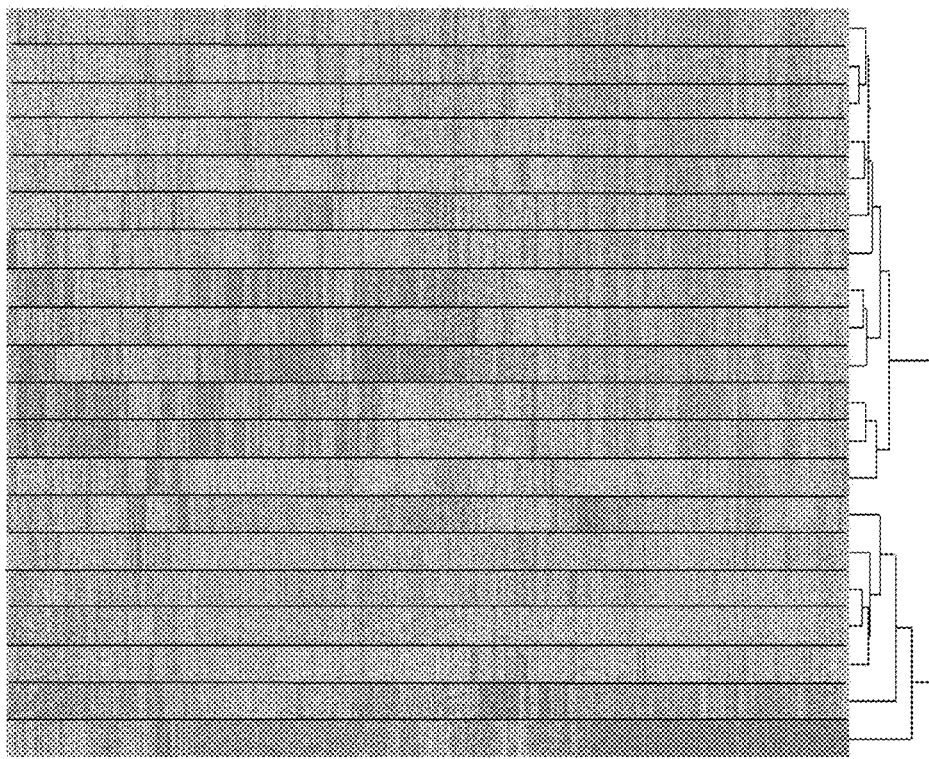
FIGS. 9A-9D: CBE effect on muscle and spinal transcriptomes of SOD1 mice.
Figure 9B:
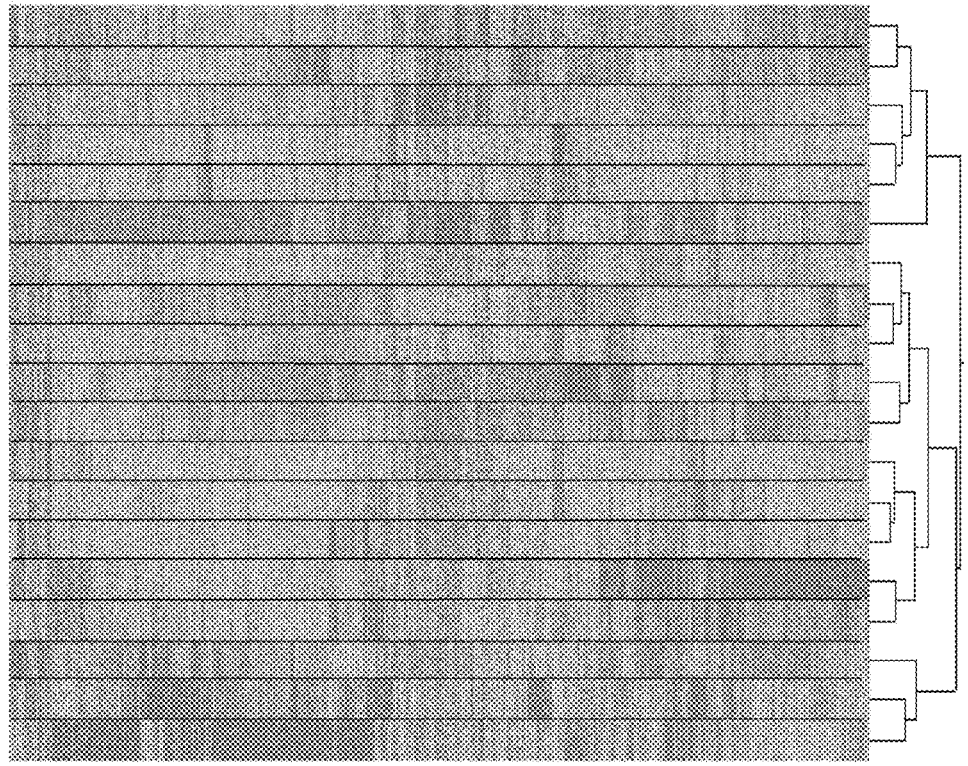
Figure 9C:
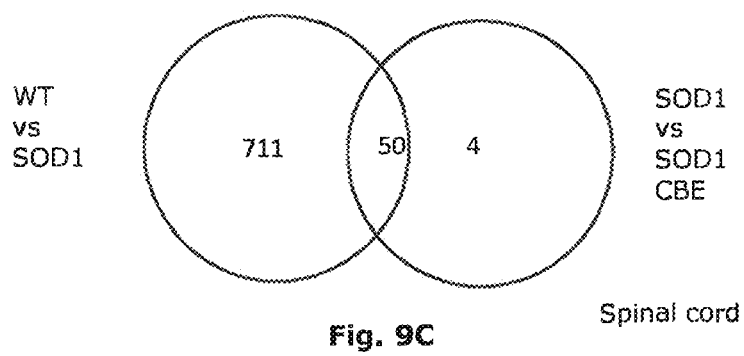
Figure 9D:
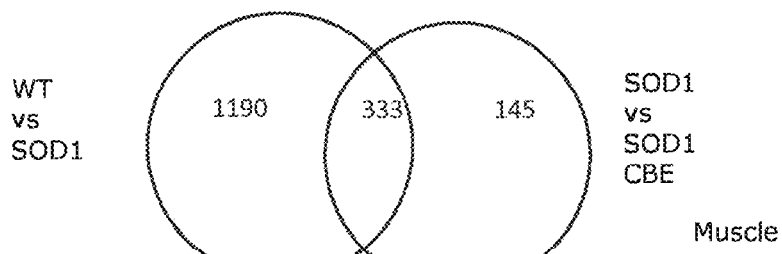

Motor unit integrity was assessed by studying neuromuscular junction integrity and motor neurons survival. At 95 days of age, neurodegeneration was detected in the lumbar spinal cord of SOD1 mice, in resulted in a loss of large motor neuron by almost 60% compared to wild type. In SOD1 mice, CBE treatment significantly mitigated the motor neuron degeneration, which was a 30% loss compared to wild type (FIGS. 6A-6B). Glial activation is a common feature in ALS and is taking part in the neurodegenerative process in SOD1 mice. The effect of CBE on astrocyte activation was assessed by quantifying the fluorescence intensity of the GFAP staining. GFAP signal was significantly stronger in SOD1 mice compared to wild type, and was comparable between the placebo and CBE treated groups, suggesting that CBE had no influence on astrocyte activation (FIG. 8).

Figure 6C:
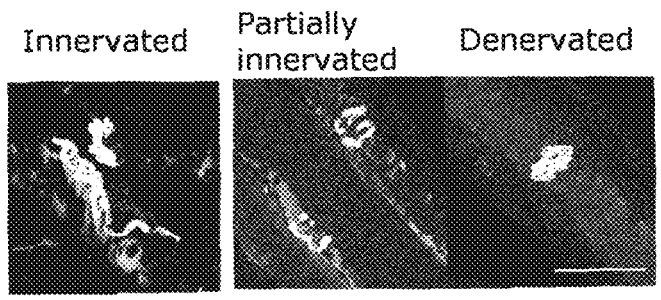
Figure 6D:
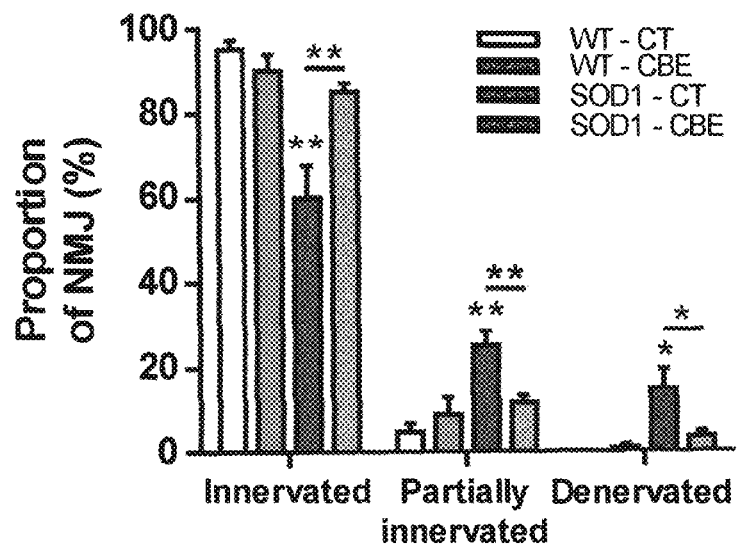

Besides preserving motor neurons from degeneration, CBE treatment preserved muscle innervation in SOD1 mice. More than 40% of neuromuscular junctions in SOD1 mice were either fully denervated or showed partial innervation, an early sign of NMJs dismantlement, at 95 days of age (FIG. 6C). After CBE treatment, SOD1 mice had a number of fully innervated NMJs comparable to wild type and significantly higher to SOD1 mice receiving the placebo (FIGS. 6C-6D).

Figure 6E:
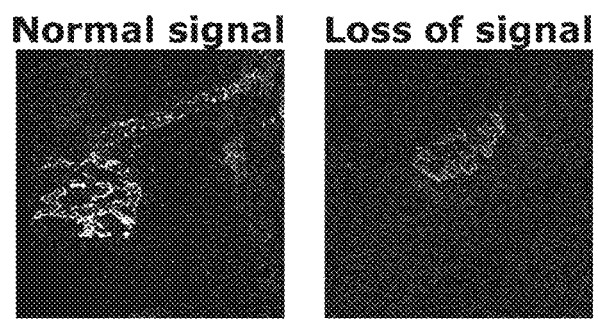
Figure 6F:
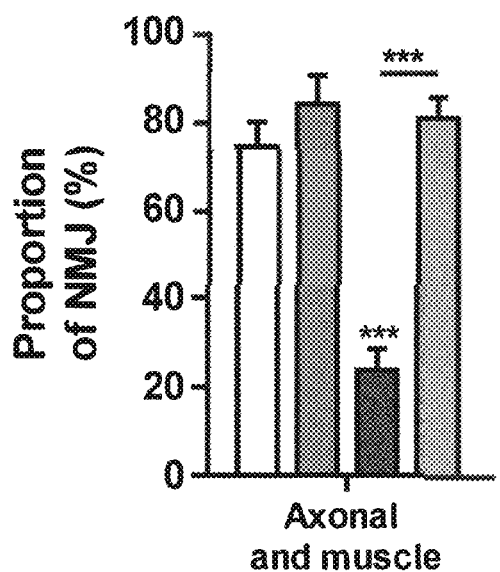

To determine whether CBE treatment had an effect on the loss of GM1a detected in muscle fibers of SOD1 mice, the number of NMJs presenting with an axonal GM1a signal were determined. In wild type mice, the majority of NMJs present with an axonal and a muscle GM1a signal. More than 75% of NMJs in SOD1 mice did not localize with an axonal signal of GM1a, whereas denervation concerns only 40% of NMJs. These results strongly suggest that loss of GM1a at the neuromuscular junction occurs before muscle denervation, as detected by the absence of neurofilament and synaptophysin close to acetylcholine receptor clusters. After CBE treatment, the presence of axonal GM1a was clearly detectable at presynaptic axons of NMJs in SOD1 mice, and was comparable to the control groups (FIGS. 6E-6F).

Example 3: CBE Stimulates Axonal Regeneration and Promote Recovery after Sciatic Nerve Injury in Non-Transgenic Mice Inhibition of GlcCer synthesis delays axonal regeneration after peripheral nerve injury (Henriques, A. et al., *Hum. Mol. Genet.*, 2015, vol 24, 7390-7405 et Dodge, J. C. et al., *Proc. Natl. Acad. Sci.*, 2015, Jun. 30; vol 112(26):8100-5), suggesting that glucosylceramide is involved in the regenerative process of axons and neuromuscular junctions. Here, we sought to determine the effect of CBE on the motor recovery after nerve injury in non-transgenic mice. CBE was administrated on a daily basis (10 mg/kg/day), from 2 days prior injury until the end of the study, 12 days after injury.

Recovery of motor functions was assessed by monitoring the time to toe spreading, interpreted as the first visible signs of re-innervation, general locomotion and motor strength. In the placebo group, toe spreading was observed around 8 days after nerve injury, and recovery of muscle strength started around 10 days after injury. At sacrifice, 12 days after injury, the locomotor profile of the placebo group showed strong reduction in the contact area and reduced hind limb step cycle of ipsilateral paw. After CBE treatment, toe spreading and muscle strength recovery occurred faster, by several days, and the locomotor profile of the injury paw was closer to the contralateral side for contact area and hindlimb step cycle. Moreover, the group receiving the CBE showed less muscle fibrillation at sacrifice, suggesting improved muscle reinnervation (FIGS. 7A-7F).

Figure 7A:
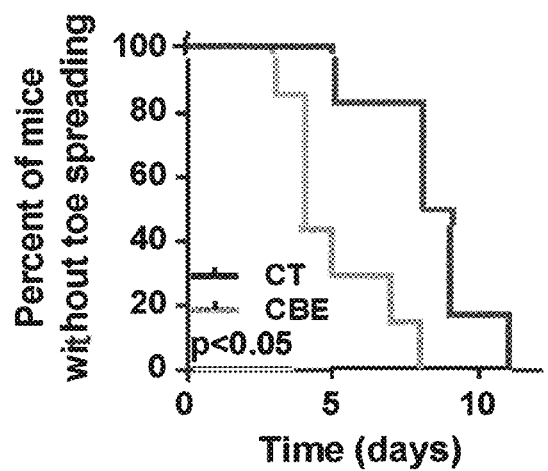
FIGS. 7A-7G: Pharmacological inhibition of glucosylceramide degradation improves functional recovery after sciatic nerve injury.
Figure 7B:
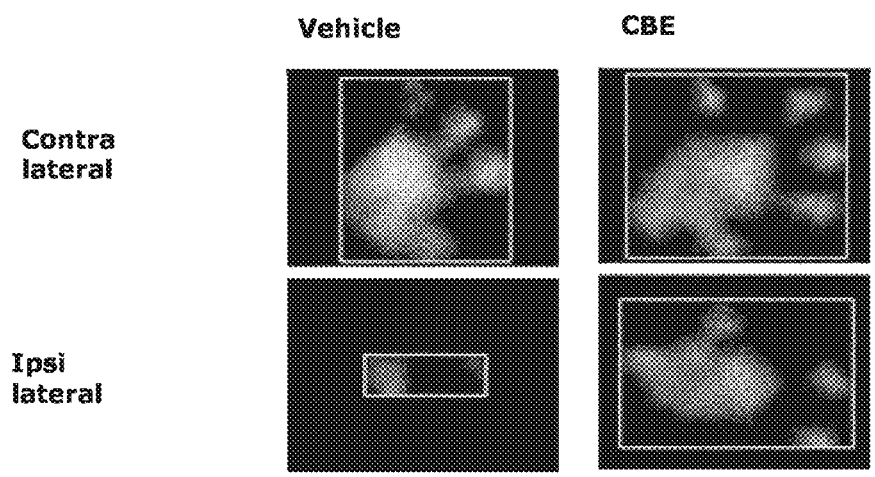
Figure 7C:
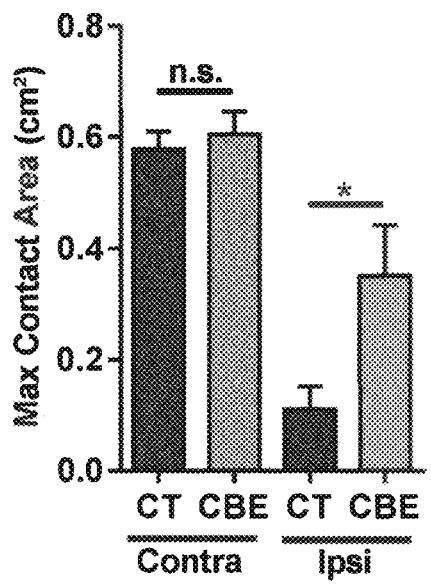
Figure 7D:
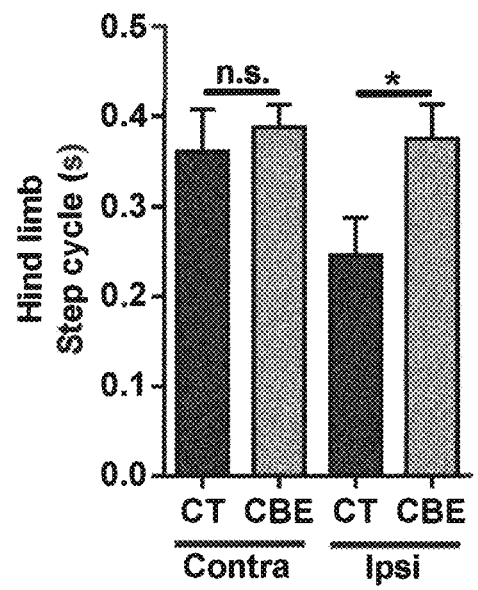
Figure 7E:
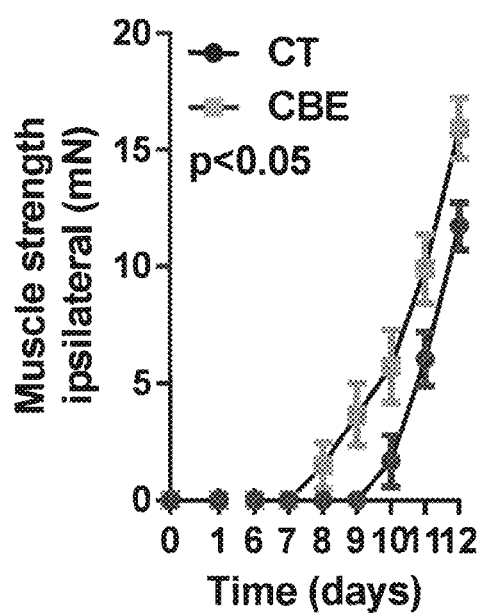
Figure 7F:
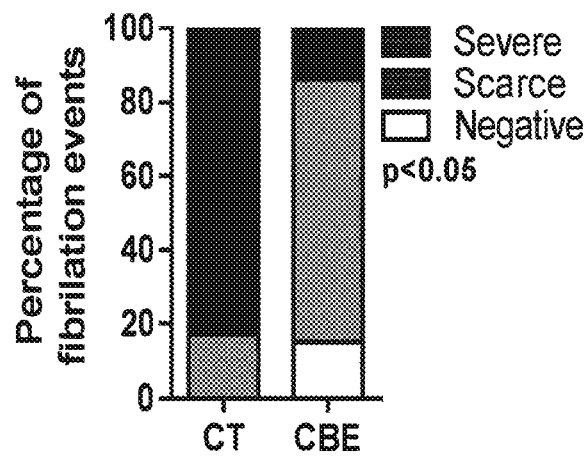
Figure 7G:
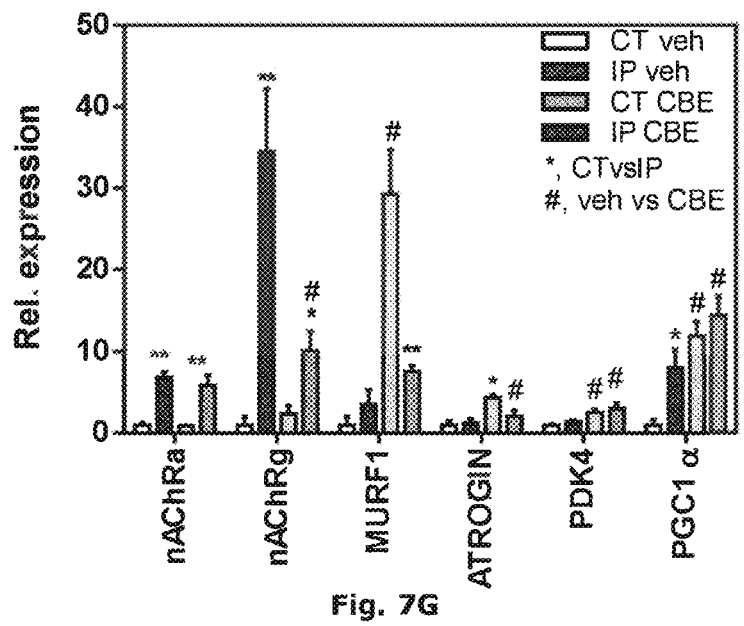

Agrin, released by axons, are essential for the expression of acetylcholine receptors at the synaptic area and their clustering. Denervation leads to the loss of axon-muscle signaling, and to the deregulation of genes such as the alpha and gamma subunits of acetylcholine receptors, energetic markers for higher oxidative capacities and activators of protein degradation pathways. At sacrifice, twelve days after injury, the upregulation of the acetylcholine receptor subunits was retrieved, as well as the stimulation of PGC1a and PDK4, promoters of lipid beta-oxidation. UPR system did not seem to deregulation 12 days after injury (FIG. 7G). CBE also partially corrected global transcriptomic deregulations in SOD1 mice (FIGS. 9A-9D) and restored the expression of genes associated with many molecular pathways relevant to ALS.

Figure 10A:
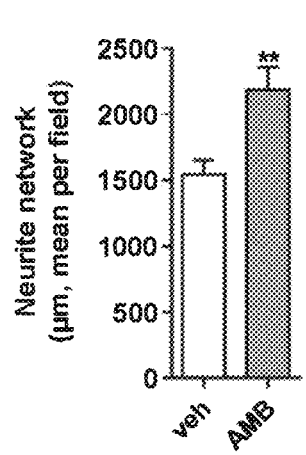
FIGS. 10A-10G: The GBA2 inhibitor ambroxol delays disease onset, improves motor functions, and extent survival in SOD1 mice FIG. 10A. Total area of innervation of functional explants under ambroxol treatment after differentiation (n=4-8/group). Mean±SEM, * p<0.05, **p<0.01
Figure 10B:
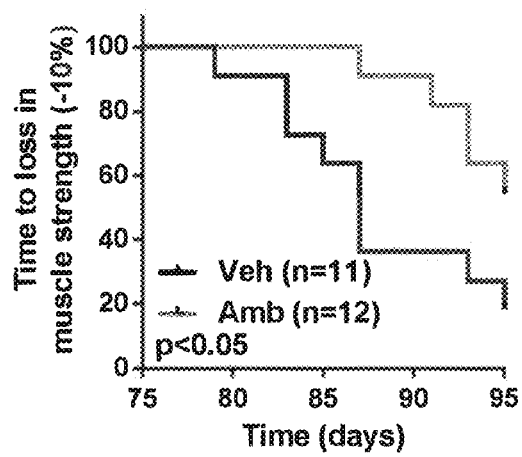
Figure 10C:
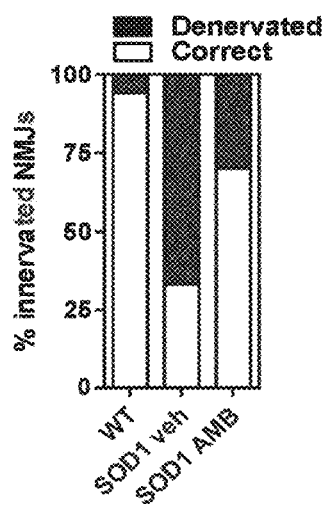
Figure 10D:
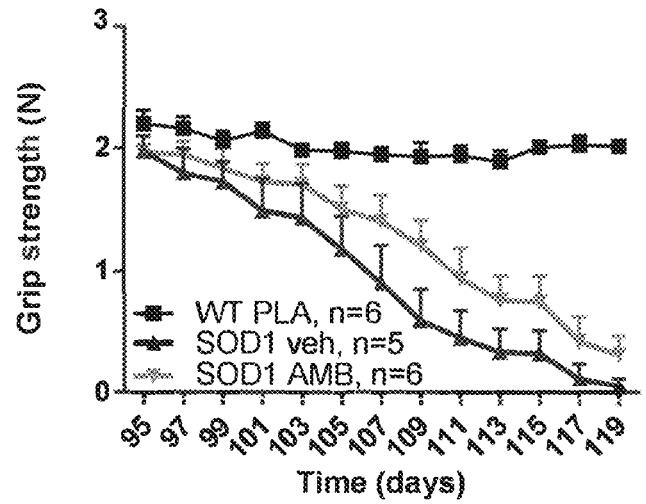
Figure 10E:
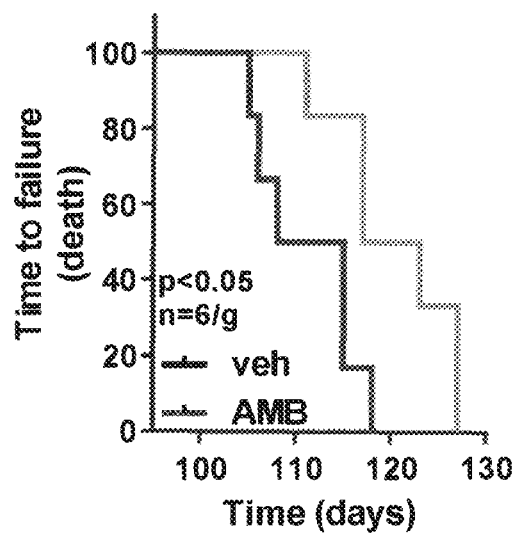
Figure 10F:
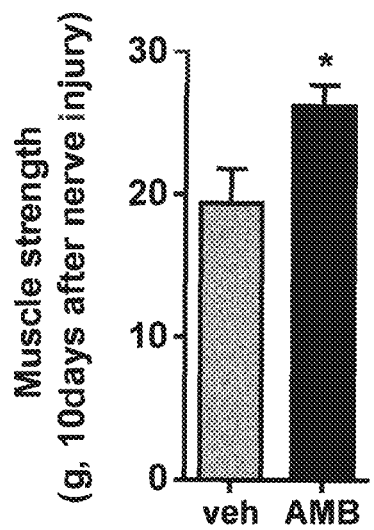
Figure 10G:
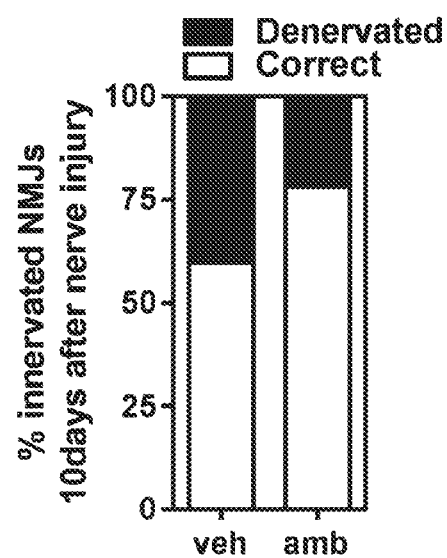

Example 4: GBA2 Inhibitor Ambroxol Delays Disease Onset, Improves Motor Functions, and Extent Survival in SOD1 Mice We next sought to determine whether another inhibitor of GlcCer degradation could support axonal plasticity and improve the phenotype of SOD1 mice. We used ambroxol, which is an inhibitor of GBA2 activity (Narita, A. et al. Ambroxol chaperone therapy for neuronopathic Gaucher disease: A pilot study. Ann. Clin. Transl. Neurol. 3, 200-215 (2016)). First, ambroxol (100 μM) was added to the culture medium of a co-culture of spinal explants and myoblasts. We found that Ambroxol improved the neurite network, suggesting that ambroxol promoted the formation of neuromuscular junctions (FIG. 10A). Next, ambroxol was given per os to SOD1 mice (120-150 mg/kg/day) from day 75 to day 95. The group of SOD1 mice receiving the placebo showed first loss of muscle strength almost 10 days earlier, as compared to SOD1 mice treated with ambroxol (FIG. 10B). Moreover, the treatment improved the innervation status (FIG. 10C). In a second cohort of mice, the treatment was initiated at disease onset to study ambroxol's effect on late disease stage and survival. Muscle strength was significantly improved after treatment (FIG. 10D) and total survival was significantly improved by more than 8 days (FIG. 10E). Next, ambroxol was given to mice subjected to sciatic nerve injury in order to determine its effects on peripheral nerve regeneration. Ambroxol significantly improved muscle strength (FIGS. 10F-10G). Moreover, ambroxol significantly improves peripheral nerve regeneration after injury (FIG. 10F) and correct muscle re-innervation (FIG. 10G).

TABLE 1

Biological functions of genes with restored expression after CBE treatment in SOD1 mice.

| Term | Biological process | Count | % | PValue |
|---|---|---|---|---|
| Spinal cord | | | | |
| GO:0045597 | positive regulation of cell differentiation | 5 | 9.6 | 0.0014 |
| GO:0051726 | regulation of cell cycle | 5 | 9.6 | 0.0029 |
| GO:0051094 | positive regulation of developmental process | 5 | 9.6 | 0.0029 |
| GO:0000165 | MAPKKK cascade | 4 | 7.7 | 0.0039 |
| GO:0007243 | protein kinase cascade | 5 | 9.6 | 0.0041 |
| GO:0007242 | intracellular signaling cascade | 8 | 15.4 | 0.0123 |
| GO:0007169 | transmembrane receptor protein tyrosine kinase signaling pathway | 4 | 7.7 | 0.0163 |
| GO:0006355 | regulation of transcription, DNA-dependent | 10 | 19.2 | 0.0174 |
| GO:0051252 | regulation of RNA metabolic process | 10 | 19.2 | 0.0191 |
| GO:0048568 | embryonic organ development | 4 | 7.7 | 0.0295 |
| GO:0006793 | phosphorus metabolic process | 7 | 13.5 | 0.0316 |
| GO:0006796 | phosphate metabolic process | 7 | 13.5 | 0.0316 |
| GO:0006468 | protein amino acid phosphorylation | 6 | 11.5 | 0.0317 |
| GO:0003006 | reproductive developmental process | 4 | 7.7 | 0.0371 |
| GO:0016310 | phosphorylation | 6 | 11.5 | 0.0482 |
| Muscle | | | | |
| GO:0044265 | cellular macromolecule catabolic process | 28 | 6.3781 | 0.0005 |

TABLE 1-continued

Biological functions of genes with restored expression after CBE treatment in SOD1 mice.

| Term | Biological process | Count | % | PValue |
|---|---|---|---|---|
| GO:0043632 | modification-dependent macromolecule catabolic process | 24 | 5.4670 | 0.0010 |
| GO:0019941 | modification-dependent protein catabolic process | 24 | 5.4670 | 0.0010 |
| GO:0009057 | macromolecule catabolic process | 28 | 6.3781 | 0.0015 |
| GO:0051603 | proteolysis involved in cellular protein catabolic process | 24 | 5.4670 | 0.0020 |
| GO:0044257 | cellular protein catabolic process | 24 | 5.4670 | 0.0021 |
| GO:0055114 | oxidation reduction | 28 | 6.3781 | 0.0022 |
| GO:0030163 | protein catabolic process | 24 | 5.4670 | 0.0033 |
| GO:0042325 | regulation of phosphorylation | 15 | 3.4169 | 0.0057 |
| GO:0007243 | protein kinase cascade | 13 | 2.9613 | 0.0068 |
| GO:0007242 | intracellular signaling cascade | 33 | 7.5171 | 0.0076 |
| GO:0051174 | regulation of phosphorus metabolic process | 15 | 3.4169 | 0.0077 |
| GO:0019220 | regulation of phosphate metabolic process | 15 | 3.4169 | 0.0077 |
| GO:0060429 | epithelium development | 13 | 2.9613 | 0.0187 |
| GO:0007167 | enzyme linked receptor protein signaling pathway | 13 | 2.9613 | 0.0196 |

REFERENCES

1. Brooks, B. R. et al. El Escorial revisited: Revised criteria for the diagnosis of amyotrophic lateral sclerosis. 1(5), 293-99(2000).
2. Mitsumoto, H., Brooks, B. R. & Silani, V. Clinical trials in amyotrophic lateral sclerosis: Why so many negative trials and how can trials be improved? *The Lancet Neurology* 13, 1127-1138 (2014).
3. Lattante, S., Ciura, S., Rouleau, G. A. & Kabashi, E. Defining the genetic connection linking amyotrophic lateral sclerosis (ALS) with frontotemporal dementia (FTD). *Trends in Genetics* 31, 263-273 (2015).
4. Schmitt, F., Hussain, G., Dupuis, L., Loeffler, J.-P. & Henriques, A. A plural role for lipids in motor neuron diseases: energy, signaling and structure. *Front. Cell. Neurosci.* 8, 25 (2014).
5. Dupuis, L. et al. Dyslipidemia is a protective factor in amyotrophic lateral sclerosis. *Neurology* 70, 1004-1009 (2008).
6. Wills, A.-M. et al. Hypercaloric enteral nutrition in patients with amyotrophic lateral sclerosis: a randomised, double-blind, placebo-controlled phase 2 trial. *Lancet (London, England)* 383, 2065-72 (2014).
7. Dupuis, L., Oudart, H., René, F., Gonzalez de Aguilar, J.-L. & Loeffler, J.-P. Evidence for defective energy homeostasis in amyotrophic lateral sclerosis: benefit of a high-energy diet in a transgenic mouse model. *Proc. Natl. Acad. Sci. U.S.A* 101, 11159-64 (2004).
8. Palamiuc, L. et al. A metabolic switch toward lipid use in glycolytic muscle is an early pathologic event in a mouse model of amyotrophic lateral sclerosis. *EMBO Mol. Med.* 7, 526-46 (2015).
9. Henriques, A. et al. Amyotrophic lateral sclerosis and denervation alter sphingolipids and up-regulate glucosylceramide synthase. *Hum. Mol. Genet.* 24, 7390-7405 (2015).
10. Dodge, J. C. et al. Glycosphingolipids are modulators of disease pathogenesis in amyotrophic lateral sclerosis. *Proc. Natl. Acad. Sci.* 1, 201508767 (2015).
11. Wennekes, T. et al. Glycosphingolipids—Nature, function, and pharmacological modulation. *Angewandte Chemie—International Edition* 48, 8848-8869 (2009).
12. Palmano, K., Rowan, A., Guillermo, R., Guan, J. & McJarrow, P. The role of gangliosides in neurodevelopment. *Nutrients* 7, 3891-3913 (2015).
13. Wu, G., Xie, X., Lu, Z.-H. & Ledeen, R. W. Sodium-calcium exchanger complexed with GM1 ganglioside in nuclear membrane transfers calcium from nucleoplasm to endoplasmic reticulum. *Proc. Natl. Acad. Sci. U.S.A* 106, 10829-10834 (2009).
14. Yu, R. K., Tsai, Y. T. & Ariga, T. Functional roles of gangliosides in Neurodevelopment: An overview of recent advances. *Neurochemical Research* 37, 1230-1244 (2012).
15. Ledeen, R. & Wu, G. GM1 in the nuclear envelope regulates nuclear calcium through association with a nuclear sodium-calcium exchanger. *Journal of neurochemistry* 103 Suppl, 126-134 (2007).
16. Tsai, Y.-T., Itokazu, Y. & Yu, R. K. GM1 Ganglioside is Involved in Epigenetic Activation Loci of Neuronal Cells. *Neurochem. Res.* 41, 107-115 (2016).
17. Kuwabara, S. & Yuki, N. Axonal Guillain-Barré syndrome: Concepts and controversies. *The Lancet Neurology* 12, 1180-1188 (2013).
18. Korkotian, E. et al. Elevation of intracellular glucosylceramide levels results in an increase in endoplasmic reticulum density and in functional calcium stores in cultured neurons. *J. Biol. Chem.* 274, 21673-21678 (1999).
19. Pelled, D., Shogomori, H. & Futerman, A. H. The increased sensitivity of neurons with elevated glucocerebroside to neurotoxic agents can be reversed by imiglucerase. *J. Inherit. Metab. Dis.* 23, 175-184 (2000).
20. Schwarz, A., Rapaport, E., Hirschberg, K. & Futerman, A. H. A Regulatory Role for Sphingolipids in Neuronal Growth. *J. Biol. Chem.* 270, 10990-10998 (1995).
21. Siebert, M., Sidransky, E. & Westbroek, W. Glucocerebrosidase is shaking up the synucleinopathies. *Brain* 1304-1322 (2014). doi:10.1093/brain/awu002
22. Dauer, R. & Albin, W. T. Magic shotgun for Parkinson's disease? *Brain* 137, 1274-1281 (2014).
23. Mcneill, A. et al. Ambroxol improves lysosomal biochemistry in glucocerebrosidase mutation-linked Parkinson disease cells. (2014). Brain. 2014 May; 137(5): 1481-1495.
24. Chandran, V. et al. Article A Systems-Level Analysis of the Peripheral Nerve Intrinsic Axonal Growth Program Article A Systems-Level Analysis of the Peripheral Nerve Intrinsic Axonal Growth Program. *Neuron* 89, 956-970 (2016).
25. Inokuchi, J. Neurotrophic and neuroprotective actions of an enhancer of ganglioside biosynthesis. Advances in Neuropharmacology; 2009; 85; 319-36 (Elsevier Inc., 2009).
26. Martin, E. et al. Loss of function of glucocerebrosidase GBA2 is responsible for motor neuron defects in hereditary spastic paraplegia. *Am. J. Hum. Genet.* 92, 238-244 (2013).
27. Sultana, S. et al. Lack of enzyme activity in GBA2 mutants associated with hereditary spastic paraplegia/cerebellar ataxia (SPG46). *Biochem. Biophys. Res. Commun.* 465, 35-40 (2015).

28. Blennow, K. et al. Gangliosides in cerebrospinal fluid in 'probable Alzheimer's disease'. *Arch Neurol* 48, 1032-1035 (1991).
29. Blennow, K. et al. Differences in cerebrospinal fluid gangliosides between 'probable Alzheimer's disease' and normal aging. *Aging (Milano.)* 4, 301-306 (1992).
30. Narita, A. et al. Ambroxol chaperone therapy for neuronopathic Gaucher disease: A pilot study. *Ann. Clin. Transl. Neurol.* 3, 200-215 (2016).

The invention claimed is:

1. A method for the treatment of a disease of the motor units, wherein the disease is Amyotrophic Lateral Sclerosis (ALS), and wherein the method comprises administering to a patient in need thereof a pharmaceutical composition consisting of ambroxol and/or a pharmaceutically acceptable salt thereof and at least one pharmaceutically acceptable carrier.

2. The method according to claim 1 wherein the pharmaceutical composition is administered to the patient at a dose of 0.01 to 500 mg/kg of body weight/day.

3. The method according to claim 1 wherein the pharmaceutical composition is administered to the patient at a dose of 0.1 to 250 mg/kg of body weight/day.

* * * * *